United States Patent
Karlsson et al.

(10) Patent No.: US 9,763,610 B2
(45) Date of Patent: Sep. 19, 2017

(54) SYSTEM AND METHOD FOR CONTINUOUSLY MONITORING AND PRESENTING BODY SUBSTANCES

(75) Inventors: Anton Karlsson, Enskede (SE); Anders Carlsson, Uppsala (SE); Andreas Broman, Sollentuna (SE)

(73) Assignee: MAQUET CRITICAL CARE MB, Solna (SE)

( * ) Notice: Subject to any disclaimer, the term of this patent is extended or adjusted under 35 U.S.C. 154(b) by 1046 days.

(21) Appl. No.: 13/519,943

(22) PCT Filed: Dec. 22, 2010

(86) PCT No.: PCT/SE2010/051458
§ 371 (c)(1),
(2), (4) Date: Oct. 19, 2012

(87) PCT Pub. No.: WO2011/081597
PCT Pub. Date: Jul. 7, 2011

(65) Prior Publication Data
US 2013/0041242 A1    Feb. 14, 2013

Related U.S. Application Data

(60) Provisional application No. 61/291,223, filed on Dec. 30, 2009.

(30) Foreign Application Priority Data

Dec. 30, 2009   (SE) ........................... 0951037

(51) Int. Cl.
  A61B 5/145    (2006.01)
  A61B 5/1486   (2006.01)
  (Continued)

(52) U.S. Cl.
  CPC ...... *A61B 5/14865* (2013.01); *A61B 5/14528* (2013.01); *A61B 5/14546* (2013.01);
  (Continued)

(58) Field of Classification Search
  CPC ...... A61M 2005/1726; A61M 2205/18; A61M 2205/60; A61M 5/142; A61M 5/172;
  (Continued)

(56) References Cited

U.S. PATENT DOCUMENTS 3,588,857 A * 6/1971 Vargo et al. .............. 340/500
5,711,861 A * 1/1998 Ward ..................... C12Q 1/54
                                                    204/403.09

(Continued)

FOREIGN PATENT DOCUMENTS

WO    2008/056363 A2    5/2008
WO    2008/143943 A1    11/2008
WO    2010/002350 A1    1/2010

OTHER PUBLICATIONS

Mandak et al. Impact of cardiopulmonary bypass on peripheral tissue metabolism and microvascular blood flow, Nov. 2008, Perfusion, 23(6):339-46.*

(Continued)

*Primary Examiner* — Jacqueline Cheng
*Assistant Examiner* — Angeline Premraj
(74) *Attorney, Agent, or Firm* — Porter Wright Morris & Arthur LLP

(57) ABSTRACT

A medical monitoring unit for continuously monitoring a glucose value and a lactate value is provided. The monitoring unit comprises: a display unit, a first unit adapted to: receive a glucose/lactate/pyruvate signal based on a measured glucose/lactate/pyruvate value, transform the glucose signal into a graphically displayable glucose/lactate/pyruvate signal, and transmit the graphically displayable glu- (Continued)

cose/lactate/pyruvate signal to the display unit of the monitoring unit, and a second unit adapted to: receive a glucose/lactate/pyruvate signal based on a measured glucose/lactate/pyruvate value, transform the glucose/lactate/pyruvate signal into a graphically displayable glucose/lactate/pyruvate signal, and transmit the graphically displayable glucose/lactate/pyruvate signal to the display unit of the monitoring unit. Furthermore, a system comprising the monitoring unit, and a sensor unit for sensing glucose and/or lactate and/or pyruvate values, is provided, as well as a method for performing the steps made possible through the provided unit and method.

45 Claims, 16 Drawing Sheets

(51) Int. Cl.
  *A61B 5/00* (2006.01)
  *G06F 19/00* (2011.01)
(52) U.S. Cl.
  CPC .............. *A61B 5/412* (2013.01); *A61B 5/686* (2013.01); *A61B 5/7445* (2013.01); *G06F 19/3456* (2013.01); *A61B 2560/0276* (2013.01); *G06F 19/3406* (2013.01)
(58) Field of Classification Search
  CPC .............. A61M 5/1723; A61B 5/1427; A61B 5/14532; A61B 5/14546; A61B 5/14557; A61B 5/14528; A61B 5/14865; A61B 5/7445
  See application file for complete search history.

(56) References Cited

U.S. PATENT DOCUMENTS

| | | |
|---|---|---|
| 6,264,627 B1 | 7/2001 | Liska et al. |
| 6,346,090 B1 | 2/2002 | Liska et al. |
| 2004/0168934 A1* | 9/2004 | Schaupp et al. ............ 205/777.5 |
| 2005/0148832 A1* | 7/2005 | Reghabi .................... A61B 5/01 600/309 |
| 2007/0179356 A1* | 8/2007 | Wessel ............... A61B 5/14532 600/300 |
| 2007/0239096 A1* | 10/2007 | Keenan ............. A61B 5/14532 604/4.01 |
| 2008/0077072 A1 | 3/2008 | Keenan et al. |
| 2008/0077073 A1* | 3/2008 | Keenan ................ A61B 5/1427 604/19 |
| 2008/0105568 A1 | 5/2008 | Wu |
| 2008/0153118 A1* | 6/2008 | Quarder ............. A61B 5/14528 435/14 |
| 2009/0131861 A1 | 5/2009 | Braig et al. |
| 2009/0275815 A1 | 11/2009 | Bickoff et al. |
| 2009/0299155 A1 | 12/2009 | Yang et al. |

OTHER PUBLICATIONS

EE Times, Panel confronts multicore pros and cons, 2006, Web, Retrieved from: http://www.eetimes.com/documents.asp?doc_id=1160267.*

Mdialysis, CMAExt—RS232 or network output of data from a 600 MD analyzer, 2007, Web, Retrieved from: http://www.mdialysis.com/software/cma600-downloads.*

CMA/Microdialysis, CMA 600 Microdialysis Analyzer, 2006, Web, Retrieved from: http://biomed.au.dk/fileadmin/www.bioed.au.dk/faenotypering/Pdf/analyzer-CMA600.pdf.*

Wilson et al, Biosensors for real-time in vivo measurements, 2005, Biosensors and Bioelectronics, 20:2388-2403.*

Revzin et al, Glucose, lactate, and pyruvate biosensor arrays based on redox polymer/oxidoreductase nanocomposite thin-films deposited on photolithographically patterned gold microelectrodes, 2002, Sensors and Actuators, 81: 359-368.*

Lowery et al, A simulation study to examine the use of cross-correlation as an estimate of surface EMG cross talk, 2003, J Appl Physiol, 94: 1324-1334.*

* cited by examiner

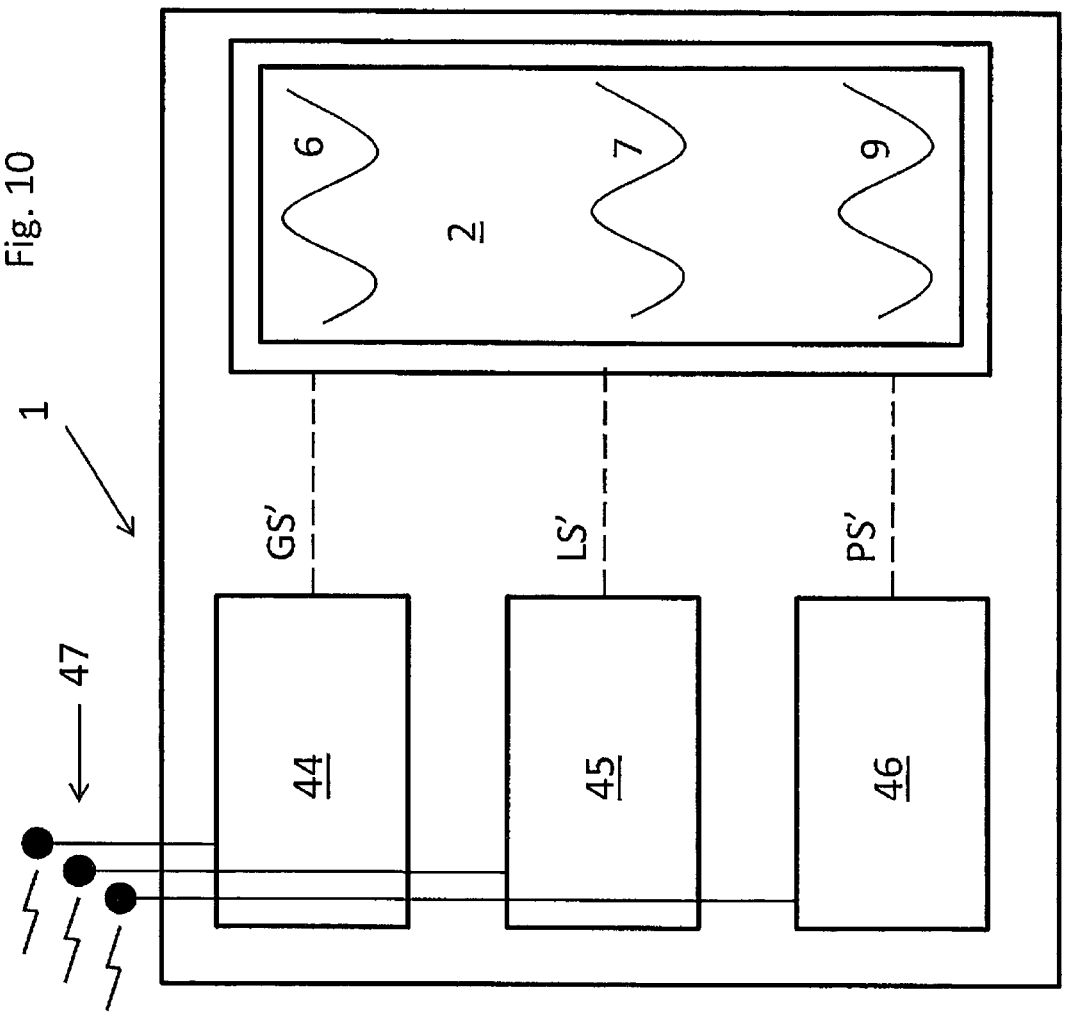
Fig. 10
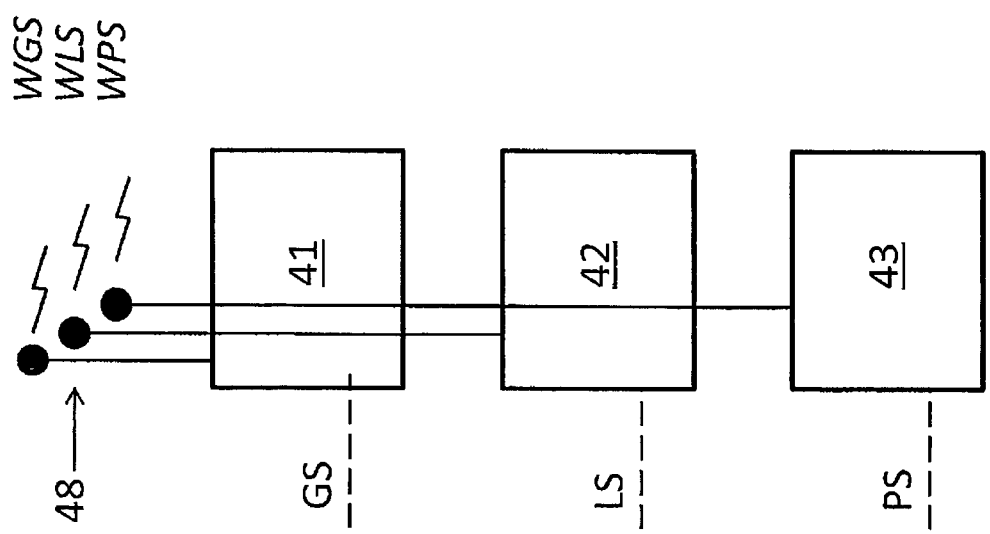

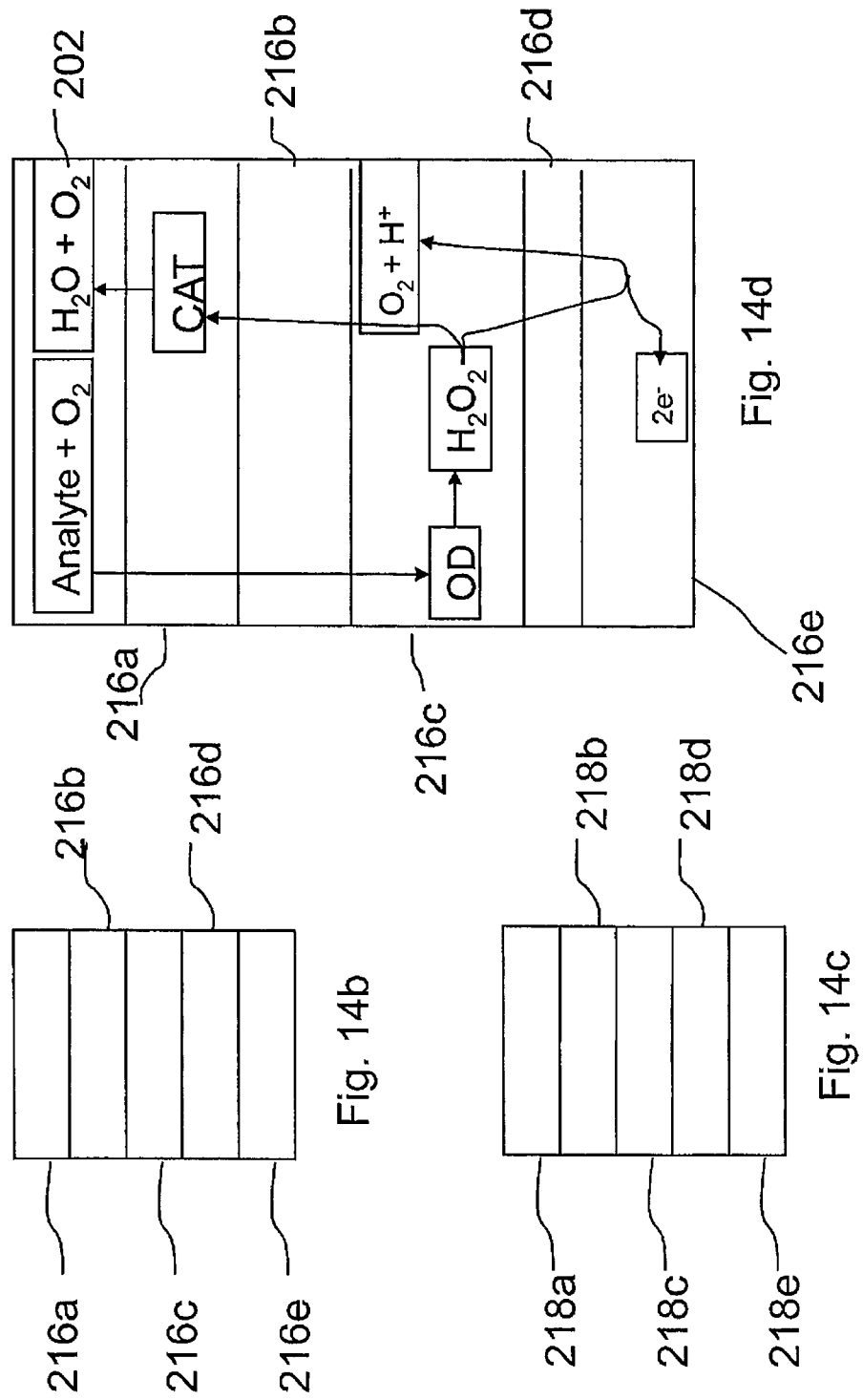

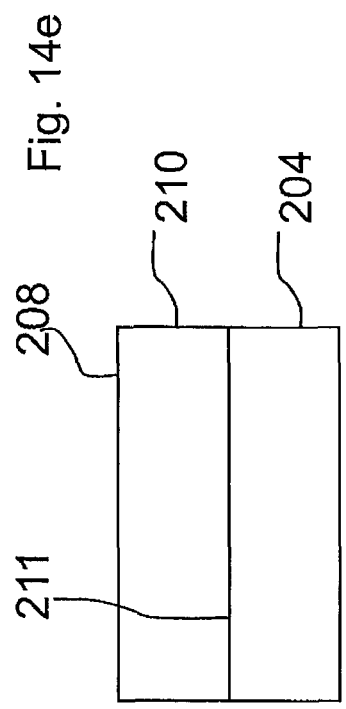
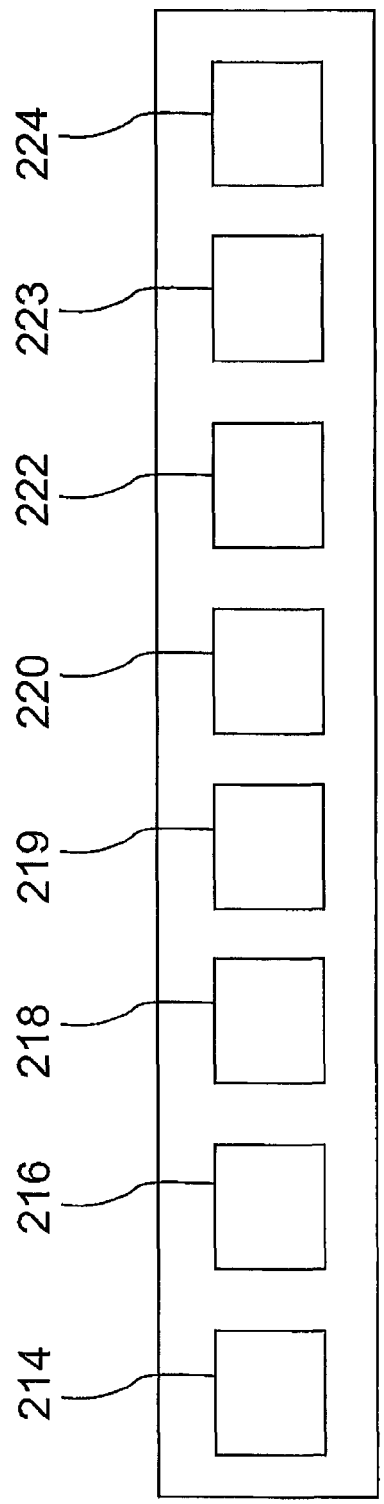

SYSTEM AND METHOD FOR CONTINUOUSLY MONITORING AND PRESENTING BODY SUBSTANCES

RELATED APPLICATION

The present application is a 371 of PCT/SE2010/051458 filed Dec. 22, 2010 and claims priority under 35 U.S.C. 119 of U.S. Application No. 61/291,223 filed Dec. 30, 2009.

TECHNICAL FIELD

The present invention relates generally to systems for continuous monitoring and/or surveillance of patients receiving medical treatment

BACKGROUND ART

Since recently it is known that certain substances that may be present in the body can function as indicators for various pathological conditions in the body. Such substances are hereafter called indicator substances. Examples of indicator substances are glucose, lactate, pyruvate, glycerol, glutamate, and glutamine and heart specific enzymes. Pathological conditions that may be indicated or detected, or as well forecasted, include ischemia, hypoglycemia sepsis, cell membrane damage or lipolysis, vasospasms and metabolic disorders. By measuring indicator substances, pathological conditions may be detected before they lead to clinical signs. It may even be possible to detect processes or conditions that eventually may lead to a pathological condition. In many cases it would be advantageous to have the possibility to measure the concentration of indicator substances directly in a blood stream, or in tissue fluid. Systems known from the background art all have different drawbacks. Examples of common drawbacks in background art systems are that the measurement delay is extensive and that one has measured phenomena that are the result of a pathological condition, e.g. ischemia. This is clearly disadvantageous. With measurement delay is meant the time that passes from the moment that a sample is taken until the moment that a measurement value relating to this sample is obtained. In background art systems measurement values can often only be obtained with relatively extended time periods. In intensive care, blood gas sample are taken on the patients as often as once every hour, however, changes in the amounts of certain substances present in the blood could happen much more rapidly than this and immediate detection is advantageous for resolving the situation and balancing the levels of the substances rapidly. In intensive care patients, the monitoring of the physiological and biochemical state is crucial.

The process of taking an arterial blood gas, in accordance with the background art, starts with the step of collecting a blood sample from an artery of the patient. The radial artery is most commonly used because of its accessibility, its ability to constrict if a bleeding occurs and since the risk of occlusion is small in the radial artery. Alternatively arteries are for example the femoral artery and the brachial artery. The femoral artery is easy to find in an acute situation, but is a larger artery, which increases the risk of complications, such as bleedings. First, the area of the skin needs to be disinfected with a disinfecting solution. Then the pulse is palpated to find a part of the artery where the pulse feels strong and where it will be easy to find it with the needle. For entering the artery, a syringe with a thin removable needle is used. The syringe contains small amounts of heparin (anticoagulants) to prevent the blood from coagulating. The needle is pricked through the skin close to your finger where the pulse is palpable and is inserted until the artery is found. Sometimes this step is difficult and repeated attempts could be necessary. When the needle hits the artery the syringe starts to fill by itself. When the syringe is fully filled the needle is separated from the syringe. A special cap is put on the syringe to prevent the syringe from leaking blood. The sample is immediately labeled. It is important that there are no air bubbles in the syringe, since it could affect the result of the analysis. Immediately thereafter the sample needs to be sent to a laboratory for analyze.

For frequently repeated blood gas sampling, such as for patients in the intensive care units, it is easier to have an arterial catheter or an arterial line, which somewhat reduces the time of obtaining a sample and the amount of times that a patient needs to be pricked. The arterial line is most often inserted into the radial artery. When a blood sample is needed a syringe is placed in the arterial catheter to collect blood. Then the syringe is then taken to a blood gas analyzer. Intensive care units usually have a blood gas analyzer located centrally in the unit. The results from the blood gas analysis are usually available after five minutes. Since a unit usually treats several patients, the blood gas procedure takes up a substantial amount of the operative staff's time. Arterial blood is usually extracted by doctors or nurses with special skills in phlebotomy.

Arterial blood gas tests, in accordance with the background art, as disclosed above, are most commonly used in the emergency room, the emergency departments and in the intensive care units. Amongst other things, it is used for acid-base balance, i.e. pH measurement, partial pressure of oxygen (PaO2), partial pressure of carbon dioxide (PaCO2) and bicarbonate level. Many blood gas analyzers will also measure lactate, glucose, hemoglobin, bilirubin and electrolytes. The pH value of the blood is an indicator of the interaction between the blood, the renal- and the respiratory system.

There are many different situations in which it is important with an arterial blood gas analyze, for example, patients with respiratory syndromes, diabetes, intoxications, kidney diseases, infections and carbon monoxide poisoning.

The systems of the background art have a several drawbacks. The formation of gas bubbles in the syringe may result in inaccurate results; the sample from a plastic syringe needs to be analyzed within 30 minutes, which hinders the operative staff from collecting a multiplicity of samples before analyzing. The process of a single blood gas analysis takes about ten minutes. Furthermore the tests are not taken frequently enough to detect sudden changes in the condition of the patient. Last but not least contact with blood is always creates risks of spreading various deceases.

SUMMARY OF INVENTION

A medical monitoring unit for continuously monitoring a glucose value and a lactate value is provided. The monitoring unit comprises: a display unit, a first unit adapted to: receive a glucose/lactate/pyruvate signal based on a measured glucose/lactate/pyruvate value, transform the glucose signal into a graphically displayable glucose/lactate/pyruvate signal, and transmit the graphically displayable glucose/lactate/pyruvate signal to the display unit of the monitoring unit, and a second unit adapted to: receive a glucose/lactate/pyruvate signal based on a measured glucose/lactate/pyruvate value, transform the glucose/lactate/pyruvate signal into a graphically displayable glucose/lactate/pyruvate signal, and transmit the graphically displayable glucose/lactate/pyruvate signal to the display unit of the monitoring unit.

According to one embodiment, the medical monitoring unit further comprises a user operable switch having a first and second state. The switch is adapted to: in the first state, enable the display unit to display the graphically displayable glucose signal, and in the second state, enable the display unit to display the graphically displayable lactate signal.

According to another embodiment the medical monitoring unit is adapted to display two different of the graphically displayable glucose/lactate/pyruvate signal and the graphically displayable glucose/lactate/pyruvate signal simultaneously.

According to yet another embodiment, the monitoring unit further comprises a user operable switch having a first, second and third state, wherein the switch is adapted to, in the first state enable the display unit to display the graphically displayable glucose signal, and wherein the switch is adapted to, in the second state, enable the display unit to display the graphically displayable lactate signal, and wherein the switch is adapted to, in the third state, enable the display unit to display the graphically displayable pyruvate signal.

The medical monitoring unit could further be adapted to display the graphically displayable glucose signal, the graphically displayable lactate signal and the graphically displayable pyruvate signal simultaneously.

The medical monitoring unit according to any of the embodiments herein could be adapted to update the graphically displayable glucose signal and/or the graphically displayable lactate signal, and/or the graphically displayable pyruvate signal with a short interval, such as every second, every 10 seconds, every minute or every 10 minutes.

According to another embodiment the monitoring unit further comprises a calculation unit adapted to: receive a glucose/lactate/pyruvate signal based on a glucose/lactate/pyruvate value, receive a different of a glucose/lactate/pyruvate signal based on a glucose/lactate/pyruvate value, calculate a first ratio based on the first signal and the second signal, transform the first ratio into a graphically displayable first ratio signal, and transmit the graphically displayable first ratio signal to the display unit of the monitoring unit.

The medical monitoring unit could further comprises an alarm system related to the first and/or second ratio, and the alarm system could be adapted to have a definable threshold value, and be adapted to be triggered by the first ratio being above, on or below the threshold value.

The medical monitoring unit could further comprise a calculation unit adapted to: receive a lactate signal based on a lactate value, receive a pyruvate signal based on a pyruvate value, calculate a second ratio based on the lactate signal and the pyruvate signal, transform the second ratio into a graphically displayable second ratio signal, and transmit the graphically displayable second ratio signal to the display unit of the monitoring unit.

According to one embodiment the medical monitoring unit comprises a glucose alarm system related to the glucose value, a lactate alarm system related to the lactate value, and/or a pyruvate alarm system related to the pyruvate value. The alarm system is adapted to have a definable threshold value, and adapted to be triggered by the glucose and/or lactate and/or pyruvate value being above, on or below the threshold value.

According to another embodiment the medical monitoring unit comprises a projected glucose alarm system related to the glucose value, a projected lactate alarm system related to the lactate value, and/or a projected pyruvate alarm system related to the pyruvate value. The projected alarm system is adapted to have a definable threshold value, and wherein the alarm system is adapted to be triggered by a projected glucose and/or lactate and/or pyruvate value being above, on or below the threshold value.

The medical monitoring unit according to any of the embodiments herein could further comprise a temperature alarm system, adapted to be triggered if a temperature value based on output from a temperature sensor is outside of a predefined interval.

According to yet another embodiment the medical monitoring unit comprises a temperature compensation unit adapted to: receive a first input signal, being a signal based on at least one of: a glucose value, a lactate value, and a pyruvate value. The temperature compensation unit is further adapted to receive a temperature signal, and calculate a temperature compensated signal on the basis of the first input signal and the temperature signal.

According to yet another embodiment, the medical monitoring unit further comprises a receiving unit for receiving wireless signals, wherein the receiving unit is adapted to: receive a wireless glucose and/or lactate and/or pyruvate signal based on a glucose/lactate/pyruvate value, transform the wireless signal to a signal, forward the signal to the first unit, receive a wireless glucose and/or lactate and/or pyruvate signal based on a glucose/lactate/pyruvate value, transform the wireless signal to a signal, and forward the signal to the second unit, According to yet another embodiment the first unit is further adapted to: receive a second glucose/lactate/pyruvate signal based on a measured value, calculate a mean glucose/lactate/pyruvate signal based on the first and second signals, transform the mean signal into a graphically displayable mean signal, and transmit the graphically displayable mean signal to the display unit of the monitoring unit.

Furthermore, a system comprising the monitoring unit according to any of the embodiments herein, and a sensor unit for sensing glucose and/or lactate and/or pyruvate values, is provided, as well as a method for performing the steps made possible through the provided unit and method.

BRIEF DESCRIPTION OF DRAWINGS

Embodiments are now described, by way of example, with reference to the accompanying drawings, in which:

FIG. 10 shows, schematically, a wireless embodiment of the monitoring unit, FIGS. 14a-f shows, schematically, an embodiment of the sensor unit.

DEFINITIONS

Figure 1:
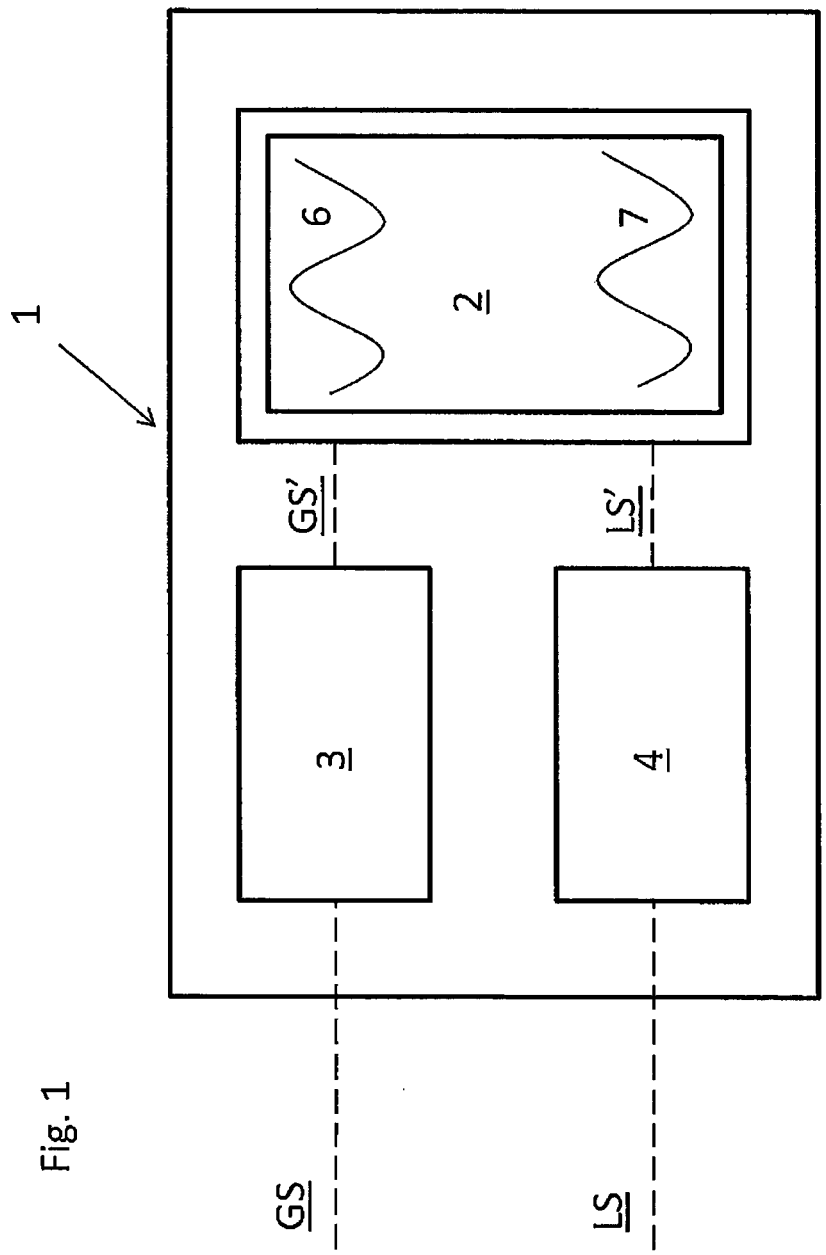
FIG. 1 shows, schematically, an embodiment of the monitoring unit.

Continuous monitoring is to be understood as monitoring with a data value with an interval shorter than 10 min, however in some embodiments the interval is shorter than 5 minutes and in some embodiments the interval is shorter than 1 minute and in some embodiments the interval is shorter than 10 seconds and in yet other embodiments the interval is shorter than 2 seconds. Shorter intervals provide more data. The more data available the more mean calculation, transformation and filtration is possible which creates a more accurate and less sensitive signal and thus a more accurate and less sensitive output signal.

Any of the monitoring/display units disclosed herein could be a bed-side monitoring/display unit adapted to be placed in proximity to a hospital bed. The bed-side unit could be a standard unit such as the units manufactured by General Electric Company, or a unit specifically adapted for the particular purpose.

The patient discussed herein is to be understood as a human or an animal patient.

The indicator substances discussed herein relates to the citric acid cycle, the details of which could for example be found in: Stryer, Lubert, *Biochemistry* $4^{th}$ ed. Pages 509-528. W.H Freeman and Company, New York.

The term "analyte" is used throughout this description to define an outflow from the probe transported to the sensor and then subsequently analysed.

The term "ultrafiltration" refers to a membrane filtration in which pressure forces a liquid against a semipermeable membrane. Suspended solids and solutes of high molecular weight are retained, while water and low molecular weight solutes pass through the membrane.

The term "probe" refers to a catheter or probe suitable to be inserted into a living body.

The term "membrane" refers to a microporous semipermeable structure.

DETAILED DESCRIPTION

According to one embodiment the monitoring system comprising the monitoring unit is provided with a microdialysis probe comprising a microdialysis membrane, both being adapted to be placed in blood or in tissue fluid. The probe is adapted to be invasively located in the body and to deliver perfusion fluid to and from the microdialysis membrane. The microdialysis probe of the system may be of the type disclosed in U.S. Pat. Nos. 6,264,627; 6,632,315; 6,346,090; 6,811,542; or in the Swedish patent application SE0602199-2. The probe dimensions may vary dependent on the selected clinical application and its location in the body. According to one embodiment the monitoring system may be a self-flowing system adapted to take advantage of the natural pressure of a pressurized body fluid, such as further disclosed in international application PCT/SE2010/051256.

The application of the monitoring unit could be for use in critical care patients, use in the emergency rooms monitoring of indication substances, such as glucose, lactate and pyruvate, use in transplantation surgery to assure the condition of the transplanted tissue or organ. In transplantation surgery the system could be used such that values from the transplanted tissue is compared with values form the central blood system, to ensure that transplanted tissue is well saturated during and after transplantation. The monitoring system could further be used to monitor a particular organ, in which case the venous outflow of an organ could be compared to the central blood system, lactate rising locally but being steady centrally is an indication of organ defect. Examples of transplantable organs which could be beneficial to monitor using the system disclosed herein is heart, liver and kidney In critical care patients vessel probing is advantageous in comparison to subcutaneous probing, since changes are much quicker displayed in the blood stream, compared to tissue. As an example, the process of administrating parenteral nutrition needs to be carefully monitored and controlled since both hypo- and hyperglycemia needs to be avoided, especially for critical care patients.

Generally, the continuous monitoring system for multiple parameters disclosed herein enables hospital staff to get instant updates on the status of indicator substances without cumbersome and delaying sampling and analyzing in a blood gas measuring equipment. Accordingly, the monitoring system admits that critical care patients can be treated more proactively which potentially can reduce treatment times and may have lifesaving consequences.

One advantage of the present system is that the condition of an organ can be efficiently supervised or monitored when e.g. surgery is being, or has been, performed on the organ. It is interesting to monitor any organ but some examples are heart, brain, liver and kidney. The system may also be used for central metabolic monitoring or peripheral arterial monitoring.

In the following a detailed description of embodiments will be given. In the drawing figures, like reference numerals designate identical or corresponding elements throughout the several figures. It will be appreciated that these figures are for illustration only and are not in any way restricting the scope. Thus, any references to direction, such as "up" or "down", are only referring to the directions shown in the figures. Also, any dimensions etc. shown in the figures are for illustration purposes.

FIG. 1 shows a schematic figure of the medical monitoring unit, according to an embodiment in which the medical monitoring unit is a monitoring unit for continuously monitoring a glucose value and a lactate value. The monitoring unit 1 comprises a display unit 2, a first unit 3 adapted to: receive a glucose signal GS based on a measured glucose value, transform said glucose signal GS into a graphically displayable glucose signal GS', and transmit said graphically displayable glucose signal GS' to the display unit 2 of the monitoring unit 1. The medical monitoring unit further comprises a second unit adapted to receive a lactate signal LS based on a measured lactate value, transform the lactate signal LS into a graphically displayable lactate signal LS', and transmit the graphically displayable lactate signal LS' to the display unit 2 of the monitoring unit 1.

The glucose and lactate values are indicator substances which are highly relevant to view in conjunction. The measuring of pyruvate is equally important and the display of which also facilitates the diagnosis and treatment of monitored patients. In the system according to FIG. 1 it is equally conceivable that the measuring of glucose or lactate is exchanged to the measuring of pyruvate, such that the monitoring unit monitors glucose and pyruvate, or lactate and pyruvate with the same general concept of simultaneously and continuously monitoring two or more interrelated indicator substances.

According to the embodiment shown in FIG. 1 the graphically displayable glucose signal GS' is displayed as a graph 6 in the display unit 2, simultaneously as the graphically displayable lactate signal LS' is displayed as a graph 7 in the display unit 2.

The graph displayed in the display unit could be displayed in conjunction with a numeric value display, or as an alternating function between displaying a numeric value and a graph, either automatically or on the basis of user input.

Due to the very low analog signal levels (low-nA or sub-nA) the analog signal is, according to one embodiment converted to a digital value as close as possible to the sensor. This will reduce the risk that the signal is influenced by external disturbances.

In any of the embodiments herein, the monitoring unit could further comprise a unit which is adapted to remove outliers, being values that are far away from the realistic glucose, lactate or pyruvate values. These outliers could be removed on the analogue signal received from a sensor, the A/D count signal and/or the value signal adapted to be displayed.

Since changes in metabolic status are comparable very slow compared with every A/D count measured, outliers in A/D counts (second based) are removed in some embodiments herein, since they are not physiological relevant. Un-physiological A/D counts much larger or smaller than the expected count are removed.

The analyte concentrations are calculated from the A/D count signals (after temperature compensation) by using response factors stored in a memory chip in the sensor unit. The response factors are determined batchwise and/or individually prior to use and programmed into the memory circuit.

Figure 2:
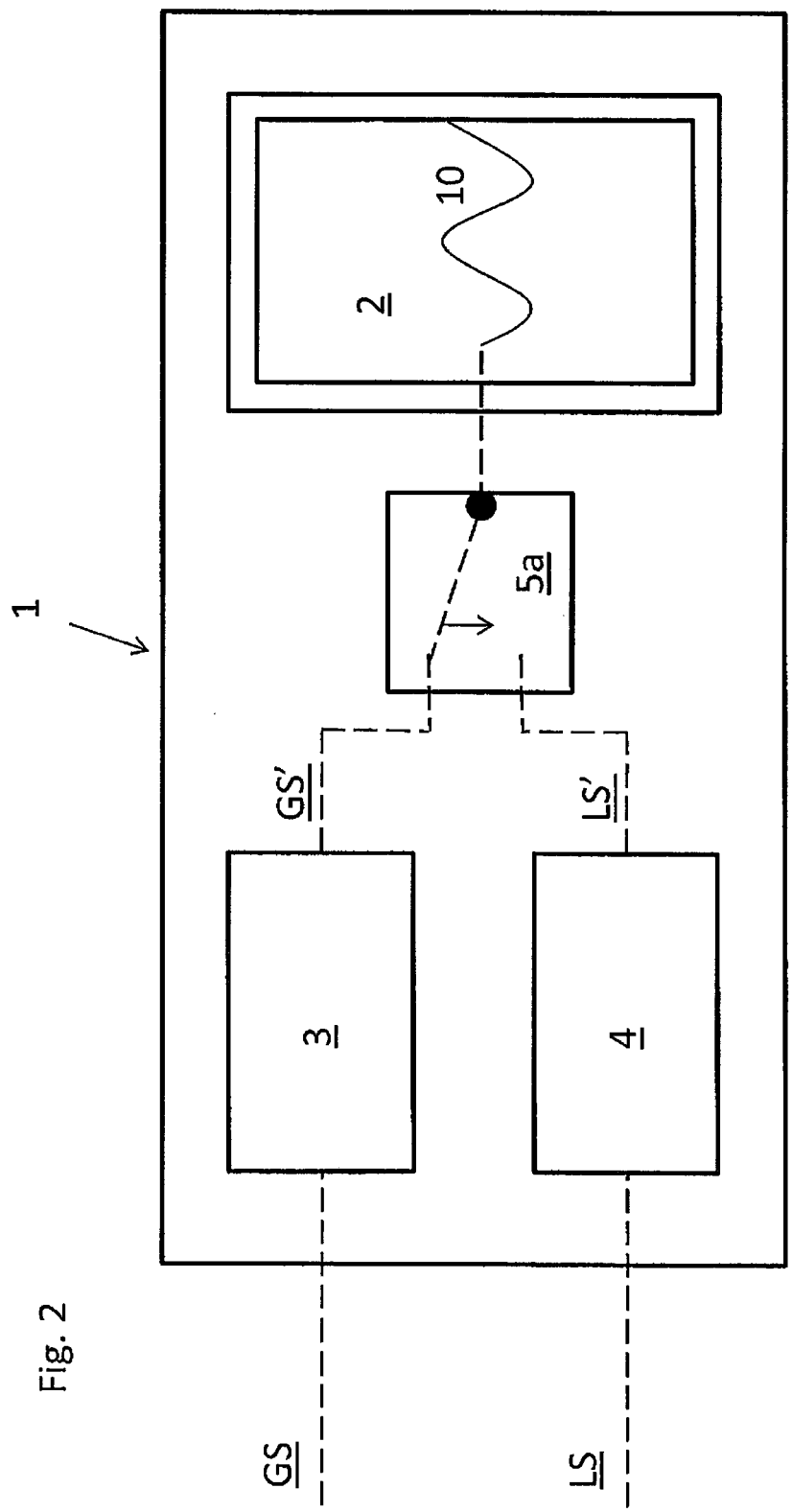
FIG. 2 shows, schematically, another embodiment of the monitoring unit.

The sensor can also be calibrated during use by entering analyte concentrations determined by an independent method, such as a blood gas analyzer, in the monitor unit and using these values to calculate the response factor used to convert the AD count signal to concentration FIG. 2 shows the medical monitoring unit according to a second embodiment in which the monitoring unit 1 further comprises a user operable switch 5a having a first and second state. The switch 5a is adapted to, in said first state, enable the display unit 2 to display the graphically displayable glucose signal GS', and in the second state enable the display unit 2 to display the graphically displayable lactate signal LS' as a graph 10. According to the embodiment shown in FIG. 2, the switch is a software implemented switch which being part of the display unit 2, which comprises a touch sensitive surface. According to other embodiments, the switch could be implemented as a button placed on or in proximity to the monitoring unit, it is also conceivable that the monitoring unit implements the function of the switch on the basis of input from a peripheral device, such as a wireless remote control or handset device.

Figure 3:
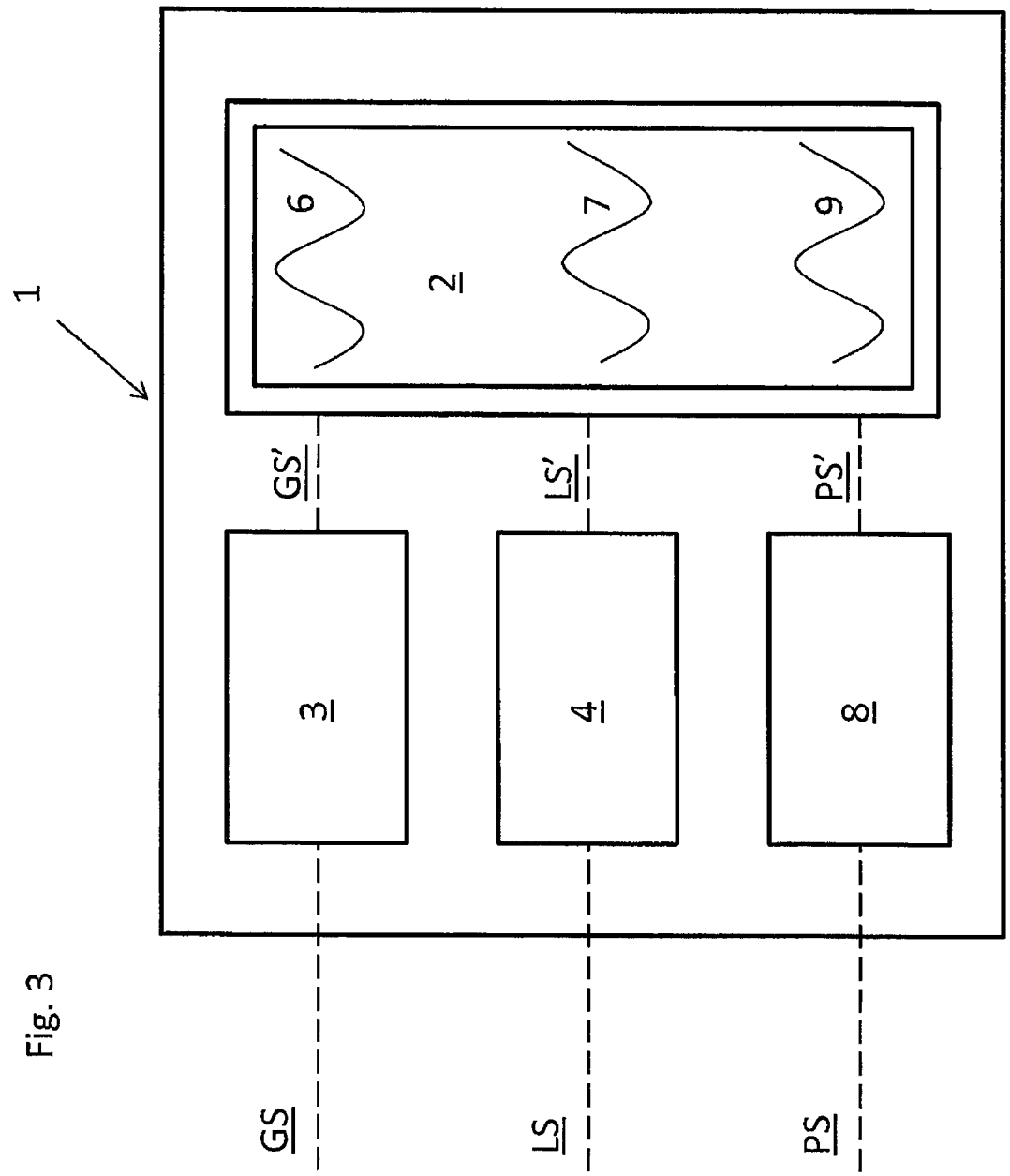
FIG. 3 shows, schematically, another embodiment of the monitoring unit.

FIG. 3 shows an embodiment of the medical monitoring unit, in which the medical monitoring unit is adapted for continuously monitoring a glucose value, a lactate value and a pyruvate value. The monitoring unit 1 comprises a display unit 2, a first unit 3 adapted to receive a glucose signal GS based on a measured glucose value, transform said glucose signal GS into a graphically displayable glucose signal GS', and transmit said graphically displayable glucose signal GS' to said display unit 2 of said monitoring unit 1. The medical monitoring unit 1 further comprises a second unit 4 adapted to receive a lactate signal LS based on a measured lactate value, transform said lactate signal LS into a graphically displayable lactate signal LS', and transmit said graphically displayable lactate signal LS' to said display unit 2 of said monitoring unit 1. The medical monitoring unit further comprises a third unit 8 adapted to receive a pyruvate signal PS based on a measured pyruvate value, transform said pyruvate signal PS into a graphically displayable pyruvate signal PS', and transmit said graphically displayable pyruvate signal PS' to said display unit 2 of said monitoring unit 1 where it is displayed as a graph 9.

According to the embodiment shown in FIG. 3 the graphically displayable glucose signal GS' is displayed as a graph 6 in the display unit 2, simultaneously as the graphically displayable lactate signal LS' is displayed as a graph 7 in the display unit 2, and simultaneously as the graphically displayable pyruvate signal PS' is displayed as a graph 7 in the display unit 2. The graph displayed in the display unit could be displayed in conjunction with a numeric value display, or as an alternating function between displaying a numeric value and a graph, either automatically or on the basis of user input.

Figure 4:
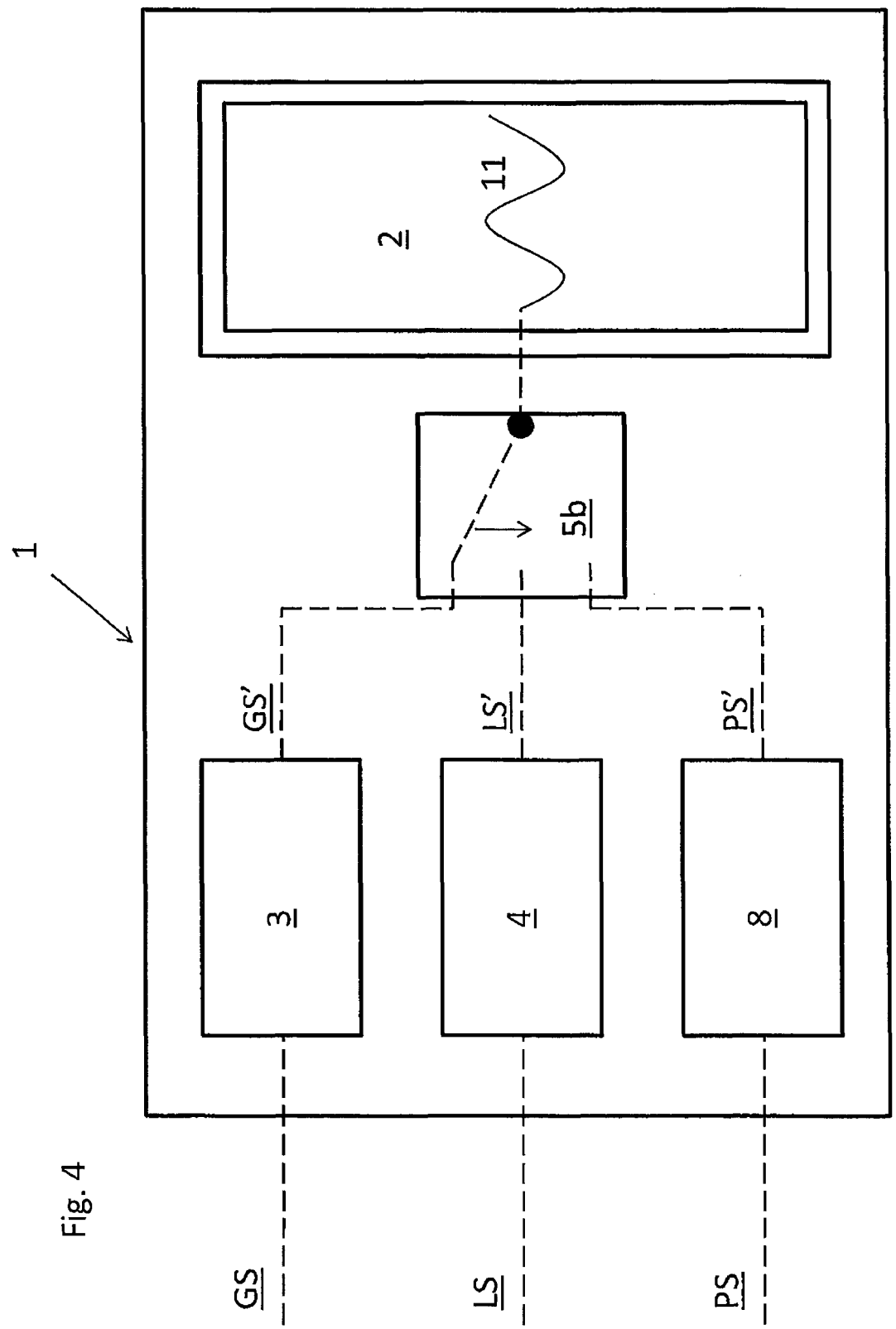
FIG. 4 shows, schematically, another embodiment of the monitoring unit.

FIG. 4 shows the medical monitoring unit according to an embodiment in which the monitoring unit 1 further comprises a user operable switch 5b having a first, second and third state. The switch 5b is adapted to, in said first state, enable the display unit 2 to display the graphically displayable glucose signal GS' as a graph 11, and in the second state enable the display unit 2 to display the graphically displayable lactate signal LS', and in the third state display the graphically displayable pyruvate signal PS'. According to the embodiment shown in FIG. 4, the switch is a software implemented switch which being part of the display unit 2, which comprises a touch sensitive surface. According to other embodiments the switch could be implemented as a button placed on or in proximity to the monitoring unit, it is also conceivable that the monitoring unit implements the function of the switch on the basis of input from a peripheral device, such as a wireless remote control or handset device.

The medical monitoring unit is according to any of the embodiments herein adapted to update the displayed glucose signal and/or lactate signal and/or pyruvate signal with a short interval. A short interval could be at least one time every second, at least one time every 10 seconds, at least one time every minute or at least one time every 10 minutes. Of importance is that the information displayed is updated so frequently that rapid and critical changes in the values can be detected fast enough for enabling suitable treatment.

Figure 5:
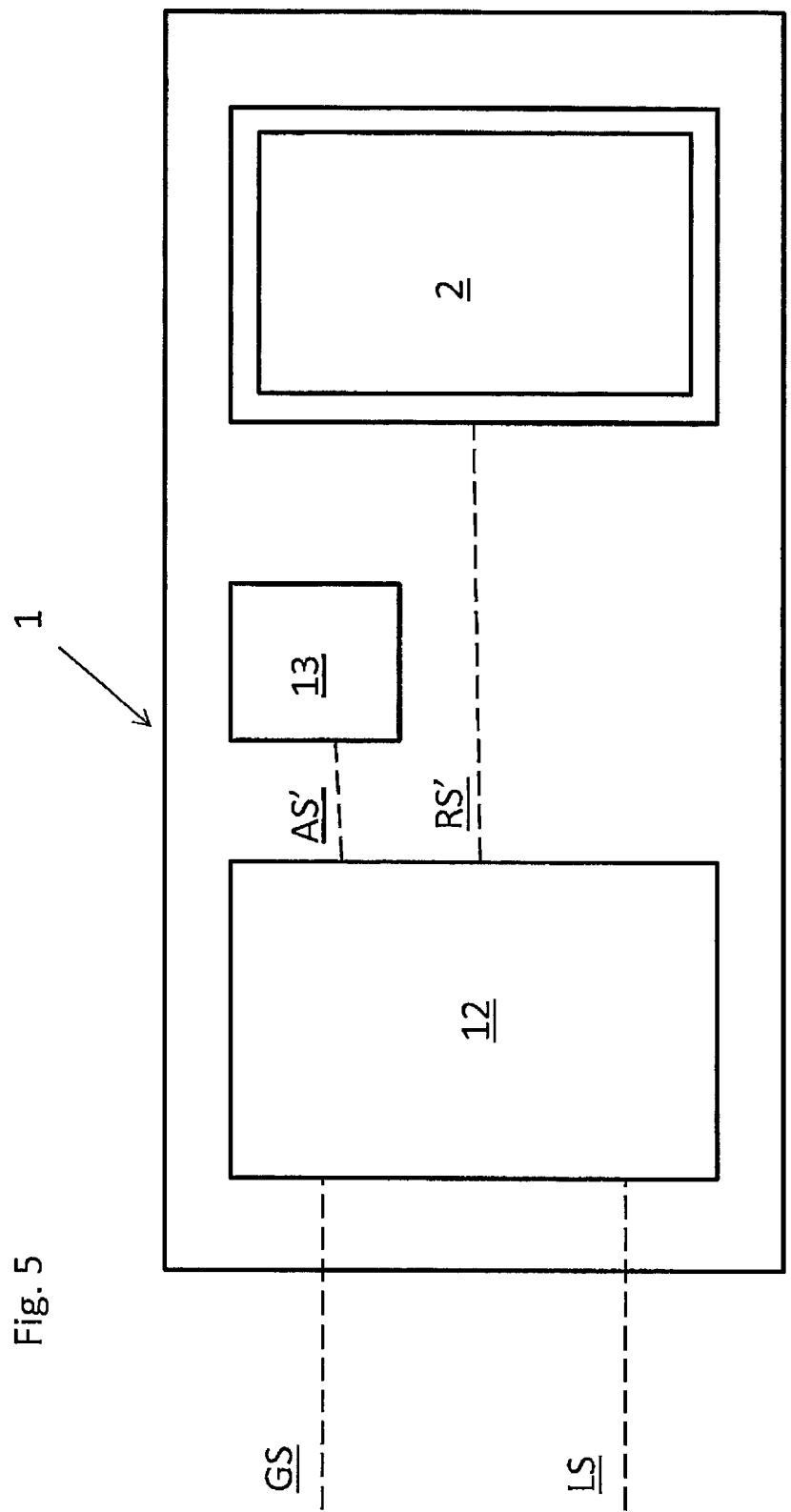
FIG. 5 shows, schematically, another embodiment of the monitoring unit.

FIG. 5 shows an embodiment of the medical monitoring unit, in which the monitoring unit 1 further comprises a calculation unit 12, which is adapted to receive a glucose signal GS based on a glucose value, receive a lactate signal LS based on a lactate value, and calculate a ratio based on said glucose signal and said lactate signal. The calculation unit 12 is further adapted to transform the ratio into a graphically displayable first ratio signal RS', and transmit the graphically displayable first ratio signal RS' to the display unit 2 of the monitoring unit. FIG. 5 further shows an alarm system 13, which is related to the ratio calculated by the calculation unit. The alarm system 13 is adapted to have a definable threshold value AS', and the alarm system 13 is adapted to be triggered by the ratio being above, on or below the threshold value.

In plastic surgery a ratio based on glucose and lactate, such as lactate/glucose or glucose/lactate is a crucial indicator of the blood flow of a free-flap, such as a piece of soft tissue. Continuously measuring and displaying this ratio could potentially increase the chance of successful transplantation.

A ratio based on lactate and pyruvate is an indicator of the amount of anaerobic metabolism, which in turn is a measure of tissue saturation. Continuously measuring and displaying this ratio could potentially reduce the risk of unobserved tissue ischemia and thus the risk of tissue death.

Figure 6:
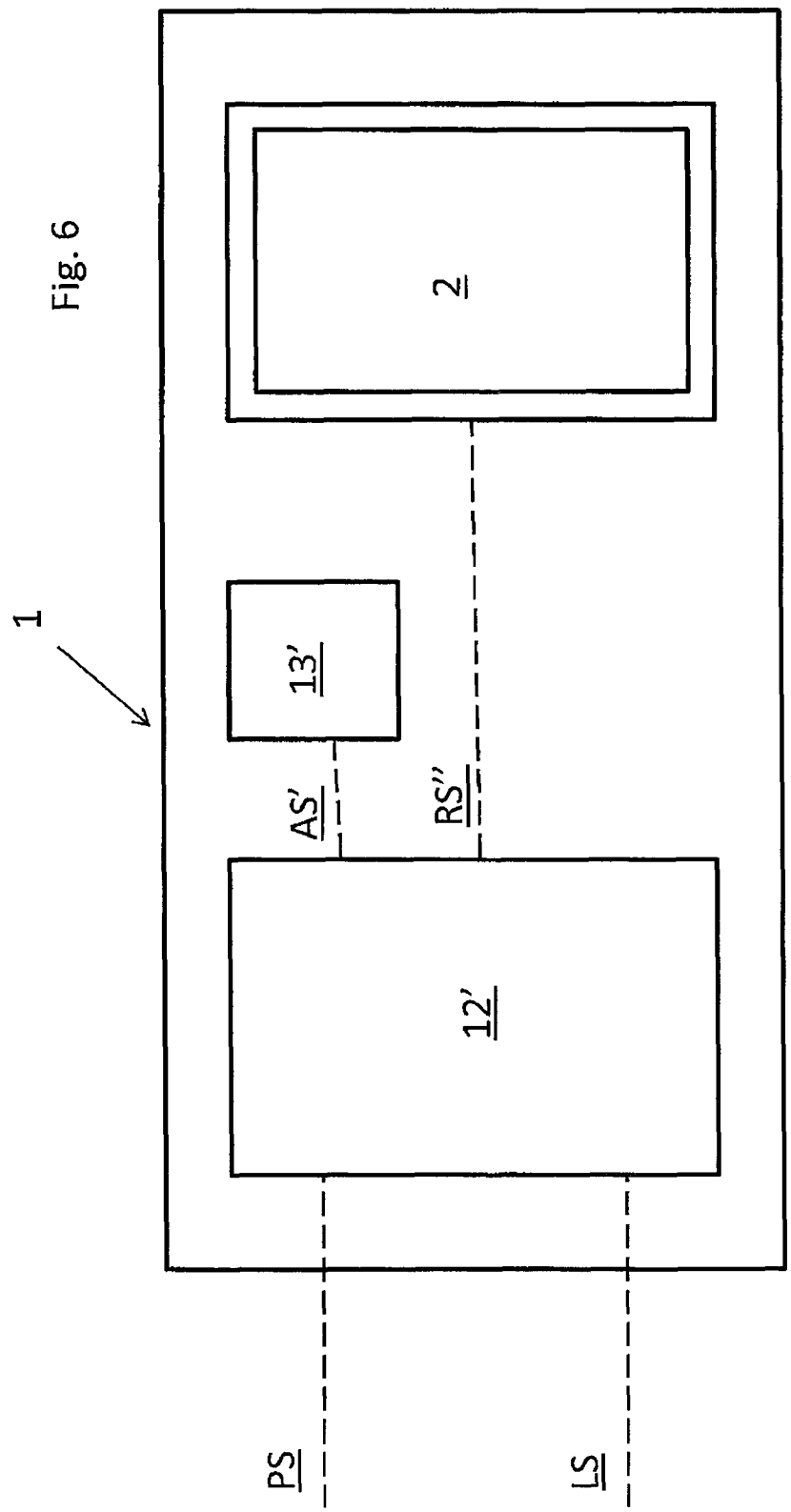
FIG. 6 shows, schematically, another embodiment of the monitoring unit.

FIG. 6 shows an embodiment of the medical monitoring unit, in which the monitoring unit 1 further comprises a calculation unit 12', which is adapted to receive a pyruvate signal PS based on a pyruvate value, receive a lactate signal LS based on a lactate value, and calculate a ratio based on said pyruvate signal and said lactate signal. The calculation unit 12' is further adapted to transform the ratio into a graphically displayable second ratio signal RS", and transmit the graphically displayable second ratio signal RS" to the display unit 2 of the monitoring unit. FIG. 6 further shows an alarm system 13', which is related to the ratio calculated by the calculation unit. The alarm system 13' is adapted to have a definable threshold value, and the alarm system 13' is adapted to be triggered by the ratio being above, on or below the threshold value.

Figure 7:
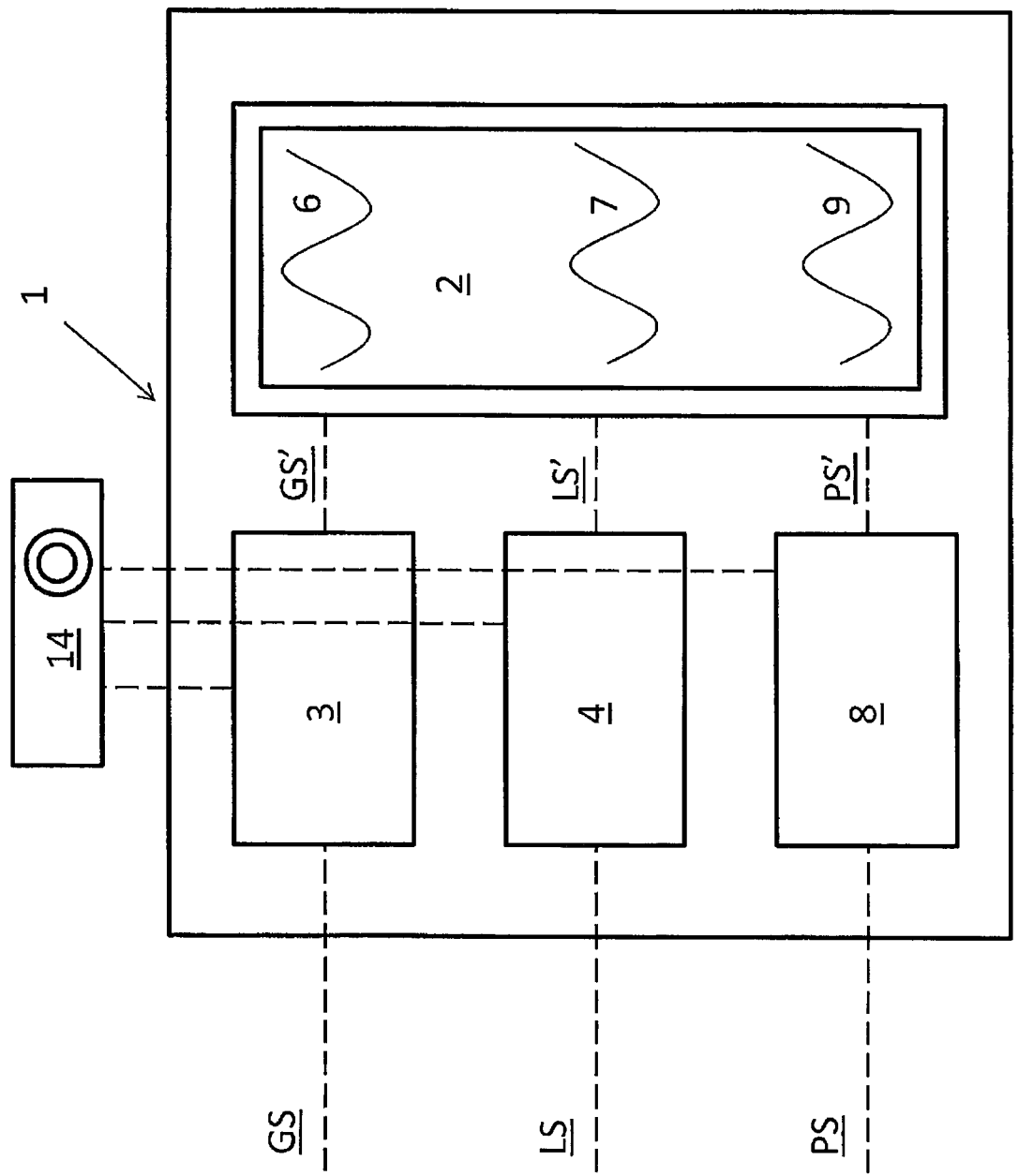
FIG. 7 shows, schematically, another embodiment of the monitoring unit.

FIG. 7 shows medical monitoring unit according an embodiment in which the medical monitoring unit further comprises an alarm system 14, being a glucose alarm system related to a glucose value, and/or a lactate alarm system related to a lactate value and/or a pyruvate alarm system related to a pyruvate value. The alarm system 14 is adapted to have a definable threshold value based on said glucose, lactate and/or pyruvate value and the alarm system 14 is adapted to be triggered by the glucose and/or lactate and/or pyruvate value being above, on or below the threshold value. The alarm systems according to any of the embodiments could be an alarm system adapted to create audio, audiovisual, visual or tactile alarms. The alarm signal could be transmitted to a central unit, such as a hospital server, for central monitoring, or the alarm system could be transmitted to mobile units, such as handsets.

Figure 8:
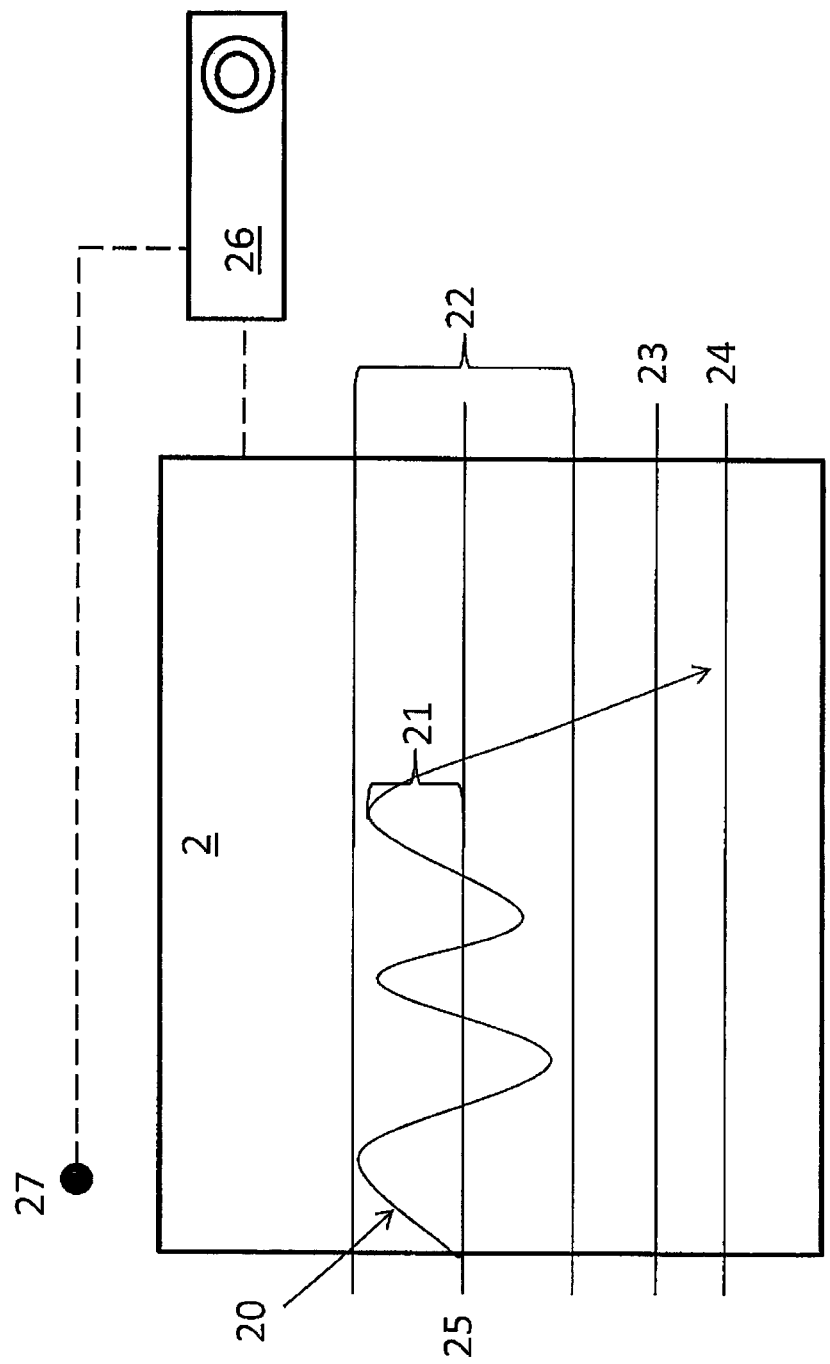
FIG. 8 shows, schematically, an embodiment of the display unit and alarming unit.

FIG. 8 shows, schematically the function of an alarm system, which could be incorporated or used with a medical monitoring unit or medical monitoring system according to any of the embodiments herein. The graph 20 represents at least one of: a glucose value, a lactate value, a pyruvate value, a glucose/lactate ratio or a lactate/pyruvate ratio. The system is adapted to incorporate a plurality of threshold values, values which could be inherent in the system or user definable. The threshold values are graphically represented by the horizontal lines crossing the display unit 2. The threshold values could, according to the embodiments shown in FIG. 8, be values set on a deviation 21 from a specified value 25, or be values based on a normal interval 22, or be values 23 which is a specific max/min value, or values 24 based on projected values. The alarm system comprises an alarming unit 26 which could be an alarming unit making an audio, audiovisual, visual or tactile alarm, such as a sounding noise and/or a flashing light and/or a vibrating handset, however it is equally conceivable that said alarming unit 26 forwards the alarm system to a central unit, such as a mainframe computer, or a wireless handset. The alarm system could be an important feature since rapid changes in the indicator substances could be very important to notice on an early stage.

Lowering of systemic Glucose can indicate Hypoglycemia. Glucose levels which are below <2.8-3 mmol/L (<50-55 mg/dL) can be dangerous and can in rare cases lead to permanent brain damage or death. A patient who is hyperglycemic can also become temporarily hypoglycemic, under certain conditions. Intensive efforts to achieve blood glucose levels close to normal have been shown to triple the risk of the most severe form of hypoglycemia, in which the patient requires assistance from by-standers in order to treat the episode.

Rising of systemic Glucose can indicate Hyperglycemia. Levels greater than 13-15 mmol/L (230-270 mg/dL) are considered high, and should be monitored closely to ensure that they reduce rather than continue to remain high. If left untreated, this can result in a variety of serious complications including organ damage. See for example G. van den Berghe et al. "Intensive insulin therapy in the critically ill patients" New England Journal of Medicine, 8 Nov. 2001; 345(19):1359-67.

Rising of systemic Lactate can indicate Sepsis. Sepsis is a serious medical condition that is characterized by a whole-body inflammatory state and the presence of a known or suspected infection.

Local increasing Lactate and lowering of Glucose/Pyruvate can indicate Ischemia. When the delivery of glucose and oxygen is reduced, there is an immediate increase of tissue Lactate and a decrease of Glucose or Pyruvate indicating signs of Ischemia. Early detection of Ischemia allows for early surgical intervention. Ischemia is defined as deficiency of blood in a part, usually due to functional construction or actual obstruction of a blood vessel According to one embodiment the medical monitoring unit comprises a projected glucose, lactate or pyruvate alarm system related to a projected glucose, lactate or pyruvate value. The projected glucose, lactate or pyruvate alarm system is adapted to have a definable threshold value (illustrated as line 24 of FIG. 8), and the alarm system is adapted to be triggered by a projected glucose, lactate or pyruvate value being above, on or below the threshold value.

FIG. 8 further shows a temperature sensor 27 which is connected to the alarming unit 26 such that the alarming unit could be triggered if a temperature value based on output from the temperature sensor 27 is outside of a predefined interval. The temperature sensor 27 could be adapted to sense the body temperature of the patient, the temperature of the analyte outside of the patient, or the temperature of the surrounding atmosphere. Since the active enzyme in the sensor unit, according to some embodiment is sensitive to temperature change, it could be of importance to continuously monitor the temperature. For some enzymes suitable for use in a sensor for use in any of the monitoring systems herein, the temperature should be within the interval 15-40c.

Figure 9:
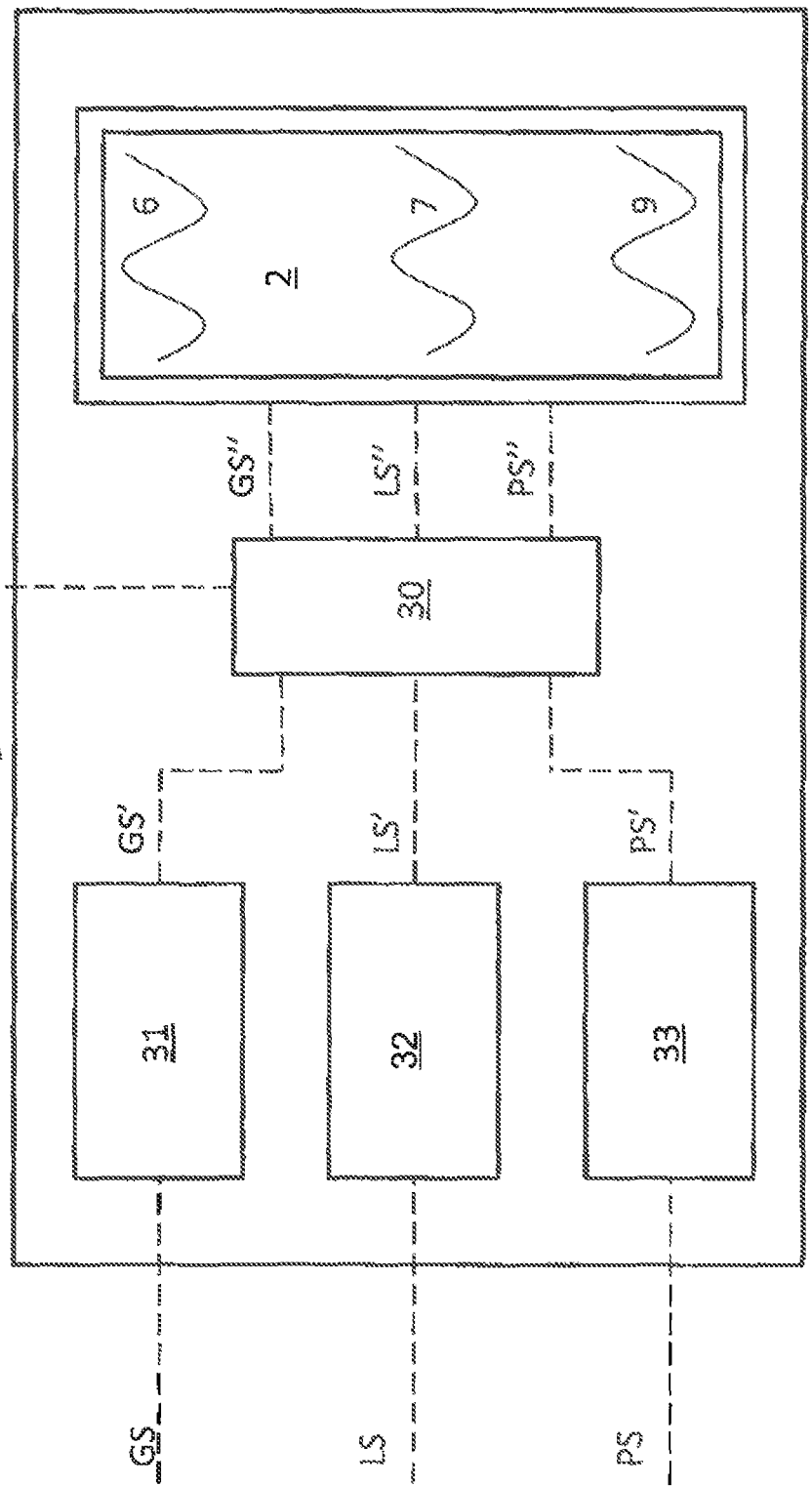
FIG. 9 shows, schematically, another embodiment of the monitoring unit.

FIG. 9 shows the medical monitoring unit 1 comprising the elements of the embodiment of FIG. 3. In the embodiment of FIG. 9, the monitoring system further comprises a temperature compensation unit 30. The medical monitoring unit is adapted to receive at least one input signal, in the shown embodiment, three analogue input signals GS, LS, PS, being signals based on a glucose value, a lactate value, and a pyruvate value. The units 31, 32, 33 transform the analogue signals into digital signals GS', LS', PS' and forward the signals to the temperature compensation unit 30. The temperature compensation unit further receives a temperature signal T from a temperature sensor 27 and calculates temperature compensated signals GS", LS" and PS", on the basis of the digital signals GS', LS', PS' and the temperature factor signal.

According to one embodiment, the temperature factors are determined batchwise prior to use and programmed into the memory circuit. The temperature factor for the different sensors varies but has the common denominator of creating an exponential error in relation to the difference in the temperature causing the error.

The diffusion rate in a measuring electrode is temperature dependent. The higher the temperature in the measuring electrode is, the higher the diffusion rate will be. This means that also the output signal from a measuring electrode is temperature dependent, the higher the diffusion rate is, the higher the output signal will be for a given concentration of the analyte in the liquid flow. It is therefore advantageous to determine the temperature of the measuring electrode to enable a correction of the output signal with respect to the determined temperature.

FIG. 10 shows the medical monitoring unit according to any of the embodiments herein, in which the medical monitoring unit 1 is adapted to receive wireless signals. The monitoring unit is at a first receiving unit 44 adapted to receive a wireless glucose signal WGS based on a glucose value, and transform the wireless glucose signal to a graphically displayable glucose signal GS', for graphically displaying said signal in said display unit. A second receiving unit 45 is adapted to receive a wireless lactate signal WLS based on a lactate value, and transform the wireless lactate signal to a graphically displayable lactate signal LS', for graphically displaying said signal in said display unit. A third receiving unit 46 is adapted to receive a wireless pyruvate signal WPS based on a pyruvate value, and transform the wireless pyruvate signal to a graphically displayable pyruvate signal PS', for graphically displaying said signal in said display unit.

The signals GS, LS, PS are first received by the external transceiver units 41, 42, 43, which units transforms the signals to wireless signals WGS, WLS, WPS, which are transmitter through a first antenna unit 48 and wirelessly to a second antenna unit 47 coupled to the receiver units 44, 45, 46. The wireless transmission could for example be digital radio transmission.

Figure 11:
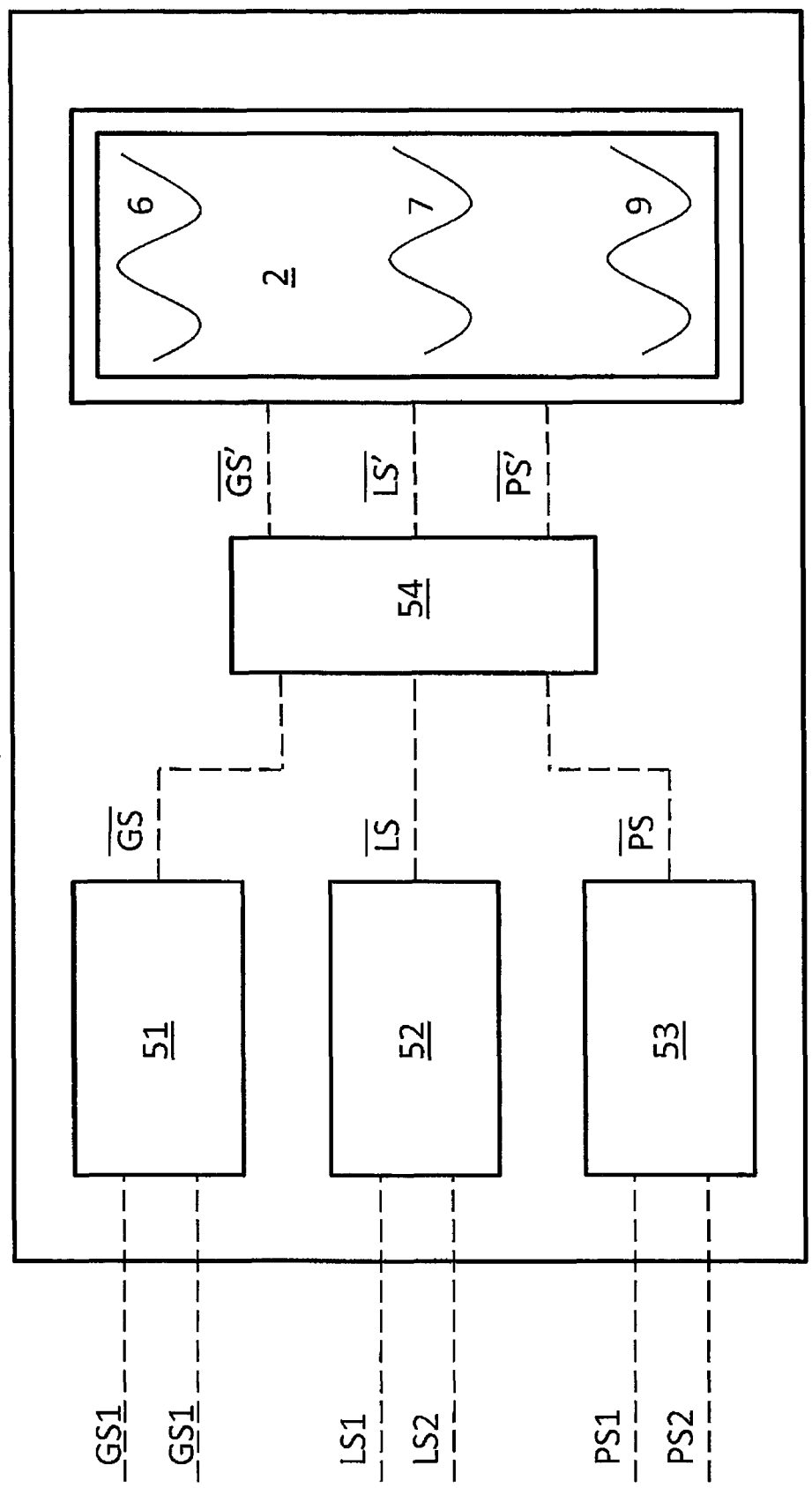
FIG. 11 shows, schematically, another embodiment of the monitoring unit.

FIG. 11 shows a medical monitoring unit 1 according to an embodiment in which the unit comprises three receiving units 51, 52, 53. The first unit 51 is adapted to receive a first and second glucose signal GS1, GS2 based on a measured glucose value, and calculate a mean glucose value $\overline{GS}$ based on the first and second glucose values GS1, GS2. The mean glucoses signal is then transferred to a transforming unit 54, which is adapted to transform the mean glucose signal $\overline{GS}$ into a graphically displayable mean glucose signal $\overline{GS'}$, and display the graphically displayable mean glucose signal $\overline{GS'}$ in a display unit 2, such as described with reference to FIG. 3. The second unit 52 is adapted to receive a first and second lactate signal LS1, LS2 based on a measured lactate value, and calculate a mean lactate value $\overline{LS}$ based on the first and second lactate values LS1, LS2. The mean lactate signal is then transferred to a transforming unit 54, which is adapted to transform the mean lactate signal $\overline{LS}$ into a graphically displayable mean lactate signal $\overline{LS'}$, and display the graphically displayable mean lactate signal $\overline{LS'}$ in a display unit 2, such as described with reference to FIG. 3. The third unit 53 is adapted to receive a first and second pyruvate signal PS1, PS2 based on a measured pyruvate value, and calculate a mean pyruvate value $\overline{PS}$ based on the first and second pyruvate values PS1, PS2. The mean pyruvate signal is then transferred to a transforming unit 54, which is adapted to transform the mean pyruvate signal $\overline{PS}$ into a graphically displayable mean pyruvate signal $\overline{PS'}$, and display the graphically displayable mean pyruvate signal $\overline{PS'}$ in a display unit 2, such as described with reference to FIG. 3.

The first and second signals discussed with reference to FIG. 11 could come from a first and second sensor, which creates redundancy in the system and makes the values more accurate, and faulty sensors are easily detected since the values between the two sensors will differ. In further embodiments it is conceivable with more than two sensors for additionally increasing the redundancy.

Figure 12:
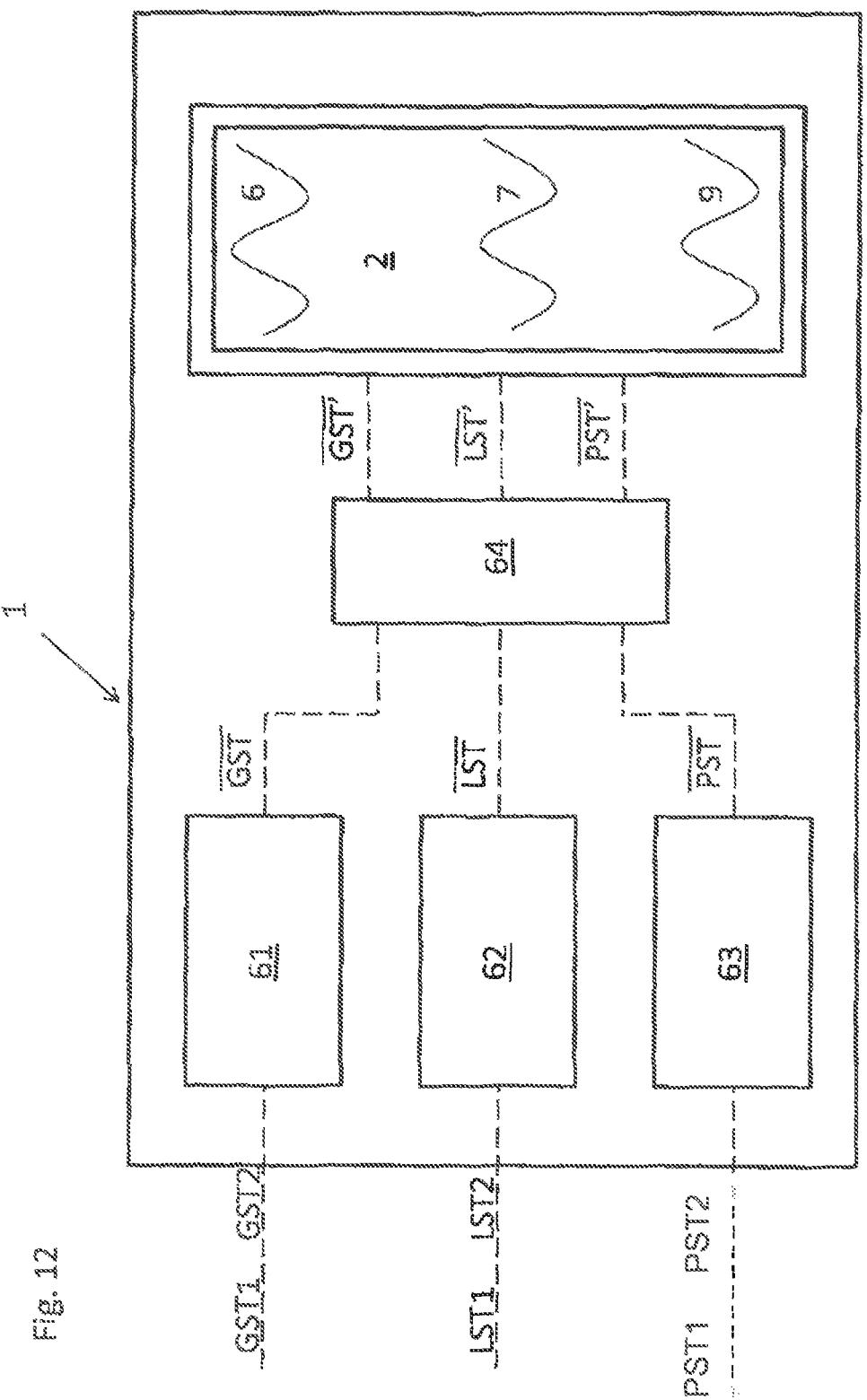
FIG. 12 shows, schematically, another embodiment of the monitoring unit.

FIG. 12 shows schematically, an embodiment in which the monitoring unit 1 comprises a first, second and third 61, 62 and 63 units. The first unit 61 is adapted to, in a first instance in time receive a first glucose signal GST1, and at a second instance in time receive a second glucose signal GST2 and perform a mean calculation transforming the first GST1 and second GST2 glucose signals to a time mean glucose signal $\underline{GST}$. The time mean glucose signal $\underline{GST}$ is transmitter to a unit 64 adapted to transform the time mean glucose signal $\underline{GST}$ to a graphically displayable time mean signal $\underline{GST'}$, which is displayed on the display unit 2 in accordance with the descriptions made with reference to FIG. 3. The second unit 62 is adapted to, in a first instance in time receive a first lactate signal LST1, and at a second instance in time receive a second lactate signal LST2 and perform a mean calculation transforming the first LST1 and second LST2 lactate signals to a time mean lactate signal $\underline{LST}$. The time mean lactate signal $\underline{LST}$ is transmitter to a unit 64 adapted to transform the time mean lactate signal $\underline{LST}$ to a graphically displayable time mean signal $\underline{LST'}$, which is displayed on the display unit 2 in accordance with the descriptions made with reference to FIG. 3. The third unit 63 is adapted to, in a first instance in time receive a first pyruvate signal PST1, and at a second instance in time receive a second pyruvate signal PST2 and perform a mean calculation transforming the first PST1 and second PST2 pyruvate signals to a time mean pyruvate signal $\underline{PST}$. The time mean pyruvate signal $\underline{PST}$ is transmitter to a unit 64 adapted to transform the time mean pyruvate signal $\underline{PST}$ to a graphically displayable time mean signal $\underline{PST'}$, which is displayed on the display unit 2 in accordance with the descriptions made with reference to FIG. 3.

In one embodiment a mean is created from further signals, which creates an even more accurate mean. An advantage of having a large amount of data is that outliers can easily be detected and be removed without affecting the output signal. Furthermore high sample rates generating a large amount of data increases the opportunities to filter and adapt the data.

Figure 13:
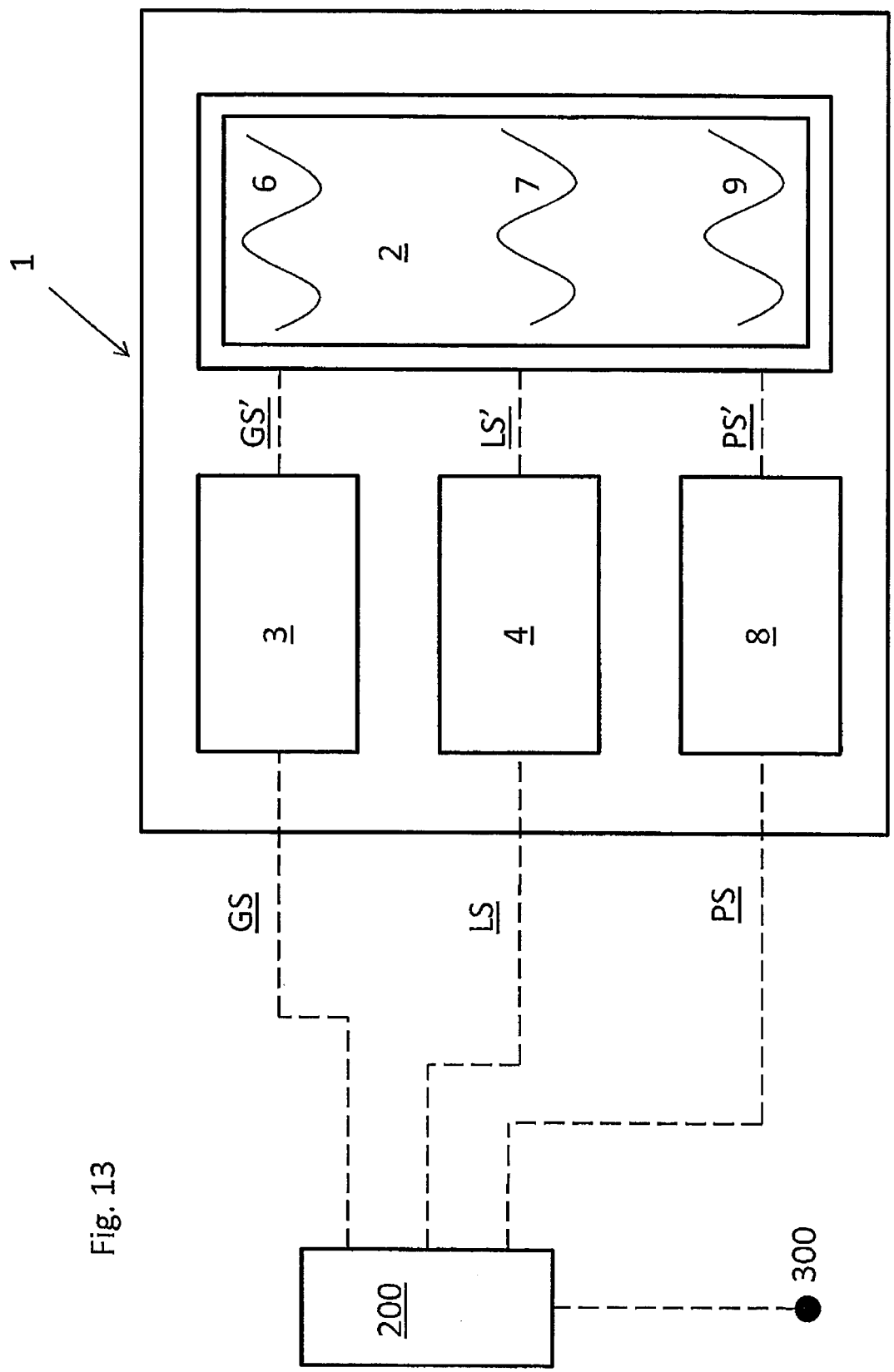
FIG. 13 shows, schematically, another embodiment of the monitoring unit.

If the sampling rate is too low, detection of physiological changes in the analyte concentrations may be delayed, which may cause delayed treatment of the patient. Furthermore, averaging and proper filtering of a larger number of data samples improves the quality of the data presented on the monitor. On the other hand, a too high sampling rate will results in a large number of data samples that needs to be processed, requiring unnecessary complex calculation and data storage unit. According to one embodiment a suitable sampling rate is in the range 0,1 to 2 Hz. FIG. 13 schematically illustrates the monitoring unit according to any of the embodiments herein, being part of a monitoring system further comprising a sensor unit 200 sensing at least one of a glucose value, a lactate value and a pyruvate value. The sensor unit 200 creates the analogue glucose signal GS, lactate signal LS and pyruvate signal PS, based on the level of glucose, lactate and pyruvate in an analyte of the patient and is in fluid connection with a probe unit 300 which is in contact with a patient. The analogue signal generated in the sensor unit is transmitted to the first second and third units 3, 4, 5, the function of which is further described with reference to FIG. 3.

The function of a sensor unit, being part of the monitoring system, will now be described The system further includes a sensor, which according to one embodiment is a flow through sensor for analysing a fluid having passed said microdialysis probe and a pump for pumping the perfusion fluid to and through the microdialysis probe and to and through the sensor. A tubing connects the pump to the microdialysis probe and the microdialysis probe to the sensor. The flow through sensor comprises a flow channel with a flow resistance or pressure drop adapted to the characteristics of the microdialysis membrane so as to eliminate, or at least substantially reduce, ultra-filtering in the microdialysis membrane. Preferably, the cross-sectional area of the flow channel is adapted to one or more microdialysis membrane characteristics including the size or diameter of the pores in the microdialysis membrane, the membrane length and the liquid permeability of the membrane.

According to one embodiment the system is a self-flowing measuring system i.e. the system does not require a pump for the collection of ultrafiltrate for continuous measurement of substances in a pressurised body fluid. In the self flowing embodiment, a measuring probe unit 300 is inserted into a pressurised body fluid of a patient. Typically, the pressurised body fluid is the blood flowing in a suitable artery of the patient, e.g. the radial artery. However, the invention is not limited to measurements of substances in arteries; a skilled person may easily modify the method to be able to perform measurements of substances in any other pressurised body fluid, e.g. any pressurised artery or vein, in the manner described. Typically, the pressure of the body fluid will be in the range of 2 to 250 mmHg.

The sensor of the measuring system includes a support 204 and at least one measuring electrode with multiple membrane layers. The layers comprise an oxidase membrane layer with immobilized oxidase enzyme, such as glucose and/or lactate oxidase, capable of reacting the analyte with oxygen in a hydrogen peroxide generating reaction; and a diffusion limiting membrane adapted to provide a higher diffusion resistance for the analyte than for oxygen and provide lower flow of analyte to the oxidase membrane layer than the conversion rate of the oxidase enzyme. In one embodiment the diffusion limiting membrane has a thickness of about 10 micrometer. The diffusion limiting membrane is according to one embodiment made from a hydrogel, preferably the hydrogel is poly-HEMA. The oxidase membrane layer has an area adapted so that the output signal of said measuring electrode is sufficiently high relative a potential noise level or noise signal for the lowest analyte concentration in the linear measurement range of the measuring electrode. The sensor further could comprise a catalase membrane with a sufficient extension and catalase activity to substantially decompose all the hydrogen peroxide reaching the membrane. The catalase membrane could have a thickness in the interval of 5 to 10 micrometer.

In one aspect of the invention, the measuring system according to any claims comprises several consecutively arranged measuring electrodes and is dimensioned according to what has previously been outlined. For example two glucose electrodes and two lactate electrodes may be arranged together with a blank electrode (without any enzyme in the oxidase membrane) which is equally dimensioned according to the outlined requirements.

Figure 14A:
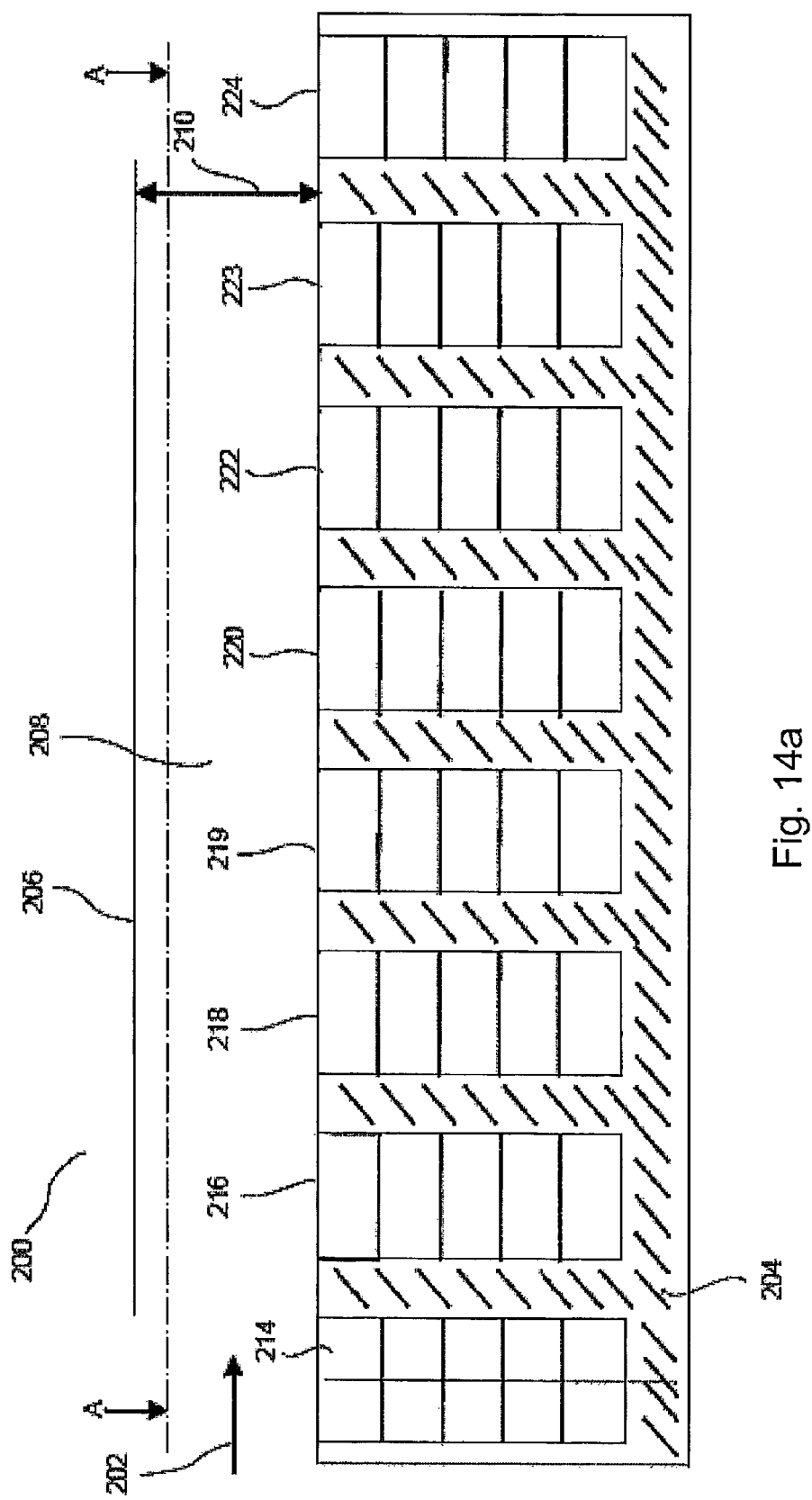

With reference to FIGS. 14a-14f, one first embodiment of the sensor 200 will be described. FIG. 14a is a drawing schematically showing a section of the sensor 200. FIGS. 14b and 14c are drawings schematically showing detailed views of the sensor electrodes 216 and 218. FIG. 14d gives a schematic view of the main reaction and transport pathways of a measuring electrode in the sensor 200. FIG. 14e is a drawing schematically showing a front view of the sensor 200, indicating the flow channel height 210 and the flow channel width 211 of the flow channel 208 formed by ceiling 206. FIG. 14f is a drawing schematically showing the sensor 200 from above, according to cut or section A-A in FIG. 14a.

The liquid flow 202 contains among other substances the analyte, e.g. glucose or lactate, and oxygen (O2). In the oxidase membrane 216c a reduction/oxidation (redox) process takes place involving the analyte and the oxygen. In this redox process the analyte is oxidized and the oxygen is reduced. The products of this process are hydrogen peroxide and the oxidation product of the analyte. The oxidation product of the analyte diffuses out to the liquid flow 202 and is washed away with the flow 202. A part of the hydrogen peroxide diffuses upwards in the measuring electrode 216 and another part diffuses towards the platinum anode 216e.

The layer 216c is in this case a lactate oxidase membrane since the measuring electrode 216 is measuring lactate. This layer is a membrane in which the enzyme lactate oxidase is immobilized, preferably the membrane is a pHEMA-hydrogel membrane (pHEMA=Poly 2-Hydroxyethylmethacrylate). In the oxidase membrane 216c the immobilized enzyme lactate oxidase acts as a catalyst when the lactate that reaches the oxidase membrane 216c reacts with oxygen and hydrogen peroxide is produced. Some of the hydrogen peroxide that is produced diffuses upwards in the direction of the enzyme-free diffusion limiting membrane 216b and the catalase membrane 216a. When this hydrogen peroxide reaches the catalase membrane 216a it is decomposed by the catalase membrane 216a into oxygen and water. The two membranes diffusion limiting membrane 216b and catalase membrane 216a are described more in detail below.

The layer 216d is a selective membrane that only is, or at least substantially only is, permeable to hydrogen peroxide. Advantageously the layer 216d is an electropolymerized permselective membrane. The selective membrane 216d is advantageous since it suppresses electrochemical interference, otherwise there would be a risk that substances other than hydrogen peroxide could reach the platinum anode 216e and give rise to erroneous readings regarding the concentration of lactate in the liquid flow 202. The hydrogen peroxide penetrates through the selective membrane 216d and is oxidised to oxygen at the platinum anode 216e. The oxidation of the hydrogen peroxide is achieved since the platinum anode 216e is polarized at an electrochemical potential where oxidation of hydrogen peroxide readily occurs (e.g. 450 mV vs Ag/AgCl reference electrode).

Hence, at the platinum anode 216e the hydrogen peroxide is detected and the amount of hydrogen peroxide detected is proportional to the amount of lactate present in the liquid flow 202. Depending on the amount of hydrogen peroxide reaching the platinum anode 216e within a certain time period, different amounts of electrons per time period is produced, and hence gives different levels of the output signal.

The layer 216b is an enzyme-free diffusion limiting membrane, advantageously a pHEMA-membrane, for controlling the diffusion of the analyte, e.g. lactate. The diffusion limiting membrane 216b controls how quickly the lactate, or how much lactate per time-period that, reaches the oxidase membrane 216c. In the liquid flow 202 the concentration of oxygen is much lower than the concentration of the analyte. One common situation is to have a concentration of 1 to 10 mmol/l of the analyte, e.g. lactate, and a concentration of 0.2 mmol/l of oxygen. If this difference in concentration would be present in the oxidase membrane 216c, there would not be enough oxygen present for the redox process in the oxidase membrane.

Therefore the diffusion limiting membrane 216b suitably reduces the diffusion speed or rate for oxygen to be 3 to 5 times lower than without the membrane 216b and suitably reduces the diffusion rate for the analyte, e.g. lactate or glucose, to be around 1000 times lower than without the membrane 216b. The reason why the diffusion limiting membrane 216b can hinder the diffusion of the analyte much stronger than the diffusion of the oxygen is that the oxygen molecules are much smaller than the molecules of the analyte. By choosing an appropriate material and thickness of the diffusion limiting membrane 216b, the above mentioned difference in limitation of diffusion rate can be achieved.

Because of this difference in reducing diffusion speed or rate the diffusion limiting membrane 216b brings the positive effect that the concentrations of oxygen and analyte is more in balance after the diffusion limiting membrane 216b, i.e. in the oxidase membrane 216c, which is desirable since it can be ensured that there is sufficient, or a surplus of, oxygen present for the redox process in the oxidase membrane 216c.

One possibility is also to have a sensor with several measuring electrodes for each measured substance, e.g. 2 or 3 measuring electrodes for lactate. In this way each measuring electrode can be optimized for a certain interval of the concentration of the analyte (e.g. glucose, lactate, pyruvate, glycerol, glutamate or glutamine) in the liquid flow. A higher thickness of the enzyme-free diffusion limiting membrane 216b makes it possible to measure higher concentrations of a substance or analyte present in the liquid flow but to measure low concentrations of a substance, the thickness of the enzyme-free diffusion limiting membrane 216b must not be too high so that the measuring electrode has the sensitivity necessary to obtain reliable measurements also for low concentrations of a substance present in the liquid flow.

The catalase membrane 216a prevents hydrogen peroxide diffusing upwards from the oxidase membrane 216c from reaching the liquid flow 202 and in this way prevents cross-talk between the different measuring electrodes. Hydrogen peroxide that reaches the catalase membrane 216a from the oxidase membrane 216c is decomposed within the catalase membrane 216a. The catalase membrane 216a also brings an extremely low flow rate dependency because hydrogen peroxide that otherwise would accumulate within the liquid flow 202 is decomposed in the catalase membrane 216a. The very low flow rate dependency is advantageous in achieving a high accuracy. If hydrogen peroxide would accumulate within the liquid flow 202, this would lead to an increase in the sensor signal measured at the platinum anode 216e. This is a problem in measuring electrodes having no catalase membrane 216a covering the oxidase membrane 216c. The flow rate dependency in those measuring electrodes makes it difficult to obtain a measuring electrode with high accuracy. If there would be no catalase membrane 216a hydrogen peroxide would accumulate in the liquid flow 202 above the measuring electrode 216 and would, at least partially, diffuse down through the measuring electrode 216 and increase the sensor signal. How much of the hydrogen peroxide accumulated in the liquid flow 202 that would diffuse down through the measuring electrode 216 would be dependent on the flow rate of the liquid flow 202. Hence, the output signal of the measuring electrode would be dependent on the flow rate of the liquid flow 202.

In the one embodiment outlined in FIG. 14a, the sensor consecutively includes a first lactate electrode arranged as described in the foregoing section of the description, a first blank electrode 214, a first lactate electrode 216, a first glucose electrode 218, a first pyruvate electrode 219 a second blank electrode 220, a second lactate electrode 222, a second glucose electrode 223 and a second pyruvate electrode 224. The first glucose electrode 218 includes layers 218a-218e and has a design similar to the first lactate electrode 216, the second lactate electrode 222 and the second glucose electrode 223 have the same design and function as the first electrodes 216 and 218 with their respective oxidases present in corresponding oxidase membranes, while including same membrane arrangements as the first lactate electrode 216. Also the first and second pyruvate electrode 219 and 224 are arranged in accordance with the first lactate electrode 216, but having pyruvate oxidase present in the oxidase membrane, suitable together with its operative cofactor thiamine pyrophosphate.

The blank electrodes 214 and 220 have a design similar to the measuring electrodes but are free from enzyme in the layers. In these layers there is only the membrane material, e.g. a hydrogel membrane, present wherein the immobilized enzymes are kept in the measuring electrodes. One reason for providing the first blank electrode 214 is to detect any hydrogen peroxide, or other electroactive substances, e.g. ascorbic acid or paracetamol, present in the liquid flow 202 already before it arrives to the measuring electrodes, in order to establish a reference level for the signals obtained from the measuring electrodes. If the output signal from the first blank electrode 214 would be very high that may be a sign of an error in the system and the output signals from the measuring electrodes obtained at that point of time can be discarded, if appropriate.

By providing two electrodes each for lactate and glucose redundancy is achieved and the reliability and accuracy of the sensor 200 is improved since if a fault arises in one measuring electrode, the other can still be used. It is more unlikely that two measuring electrodes should be erroneous than that an error occurs in one measuring electrode. By comparing the readings or sensor signals from two measuring electrodes measuring the same substance it can be determined if the measuring electrodes function correctly, or if one of them gives an erroneous reading. The possibility to detect such erroneous readings increases the accuracy of the sensor 200 since the probability to have access to a sensor signal from a properly functioning measuring electrode is increased.

One reason for providing the second blank electrode 220 is to detect any potential cross talk between the measuring electrodes. That is, e.g. to detect potential hydrogen peroxide present in the liquid flow 202 in the flow channel 208. If for example the catalase membrane of one of the first measuring electrodes would not function properly hydrogen peroxide from that measuring electrode could enter into the flow channel 208. Such a situation can be detected by comparing the signals from the first blank electrode 214 and the second blank electrode 220.

One measure for the flow channel 208 is a flow channel height 210 of approximately 75 micrometer and a flow channel width 211 of approximately 450 micrometer. A suitable interval for the flow channel width 211 is 250 to 1000 micro meters. A flow channel width 211 of 250 micrometer is a suitable lower limit since that width still renders the area of the oxidase membrane 216c sufficiently large. With a smaller flow channel width 211 than 250 micrometer problems may be encountered with a too low signal level from the sensor because resulting from a small production of hydrogen peroxide in the oxidase membrane 216c due to a too small area of the oxidase membrane 216c. This depends on the lowest analyte concentration that the measuring electrode should be able to detect with sufficient accuracy. The oxidase membrane 216c may have a circular or essentially circular shape, as seen in the direction of the arrows at "A" in FIG. 14a. In this case a suitable interval for the dimensions of the oxidase membrane is a diameter of 250-1000 micrometer, suitably 250-700 micrometer, most preferably about 450 micrometer. A flow channel width of 1000 micrometer is a suitable upper limit to limit the internal volume in the system to advantageously limit the delay in the system.

However, the system described herein is not limited to sensors detecting a current. Sensors detecting e.g. temperature, electrochemical potential or conductivity changes are also conceivable for detecting the variables described herein.

The monitoring system may comprise further units according to the embodiments described in relation to the monitoring unit. The monitoring system is to be understood as a monitoring system comprising any of the monitoring units described herein, or a combination thereof. As an example, the sensor unit [SENSOR UNIT] could comprise a wireless transmission unit adapted to wirelessly transmit the first glucose, lactate and/or pyruvate signal to the monitoring unit.

The monitoring system may also comprise any of the alarm systems described herein. Such an alarm system could be an alarm system adapted to be triggered by at least one of: a glucose level of interest, a rate of change over time of a glucose level of interest, a lactate level of interest, a rate of change over time of a lactate level of interest, a pyruvate level of interest, a rate of change over time of a pyruvate level of interest, a lactate level of interest, and a rate of change over time of a lactate level of interest.

According to one embodiment the alarm system could be triggered by a signal related to the first and second blank electrode, described with reference to FIG. 14. More precisely the alarm system could be adapted to be triggered if the difference between a first value based on an output from the first blank electrode and a second value based on an output from the second blank electrode is equal to or larger than a predefined threshold value. This particular alarm function is adapted to detect the existence of cross-talk between the first and second blank electrode, i.e. if the first blank electrode affects the second blank electrode to a degree such that it will alter the results too much. According to one embodiment the difference between the blank electrodes should be less than 0.3, i.e. the alarm is adapted to be triggered if: $b2-b1>0.3$.

According to one embodiment the alarm system could be triggered by a temperature value based on output from a temperature sensor (described with reference to FIG. 9) is outside of a predefined interval.

According to another embodiment the monitoring system further comprises an air bubble alarm system adapted to be triggered by the detection of an air bubble in the sensor or the probe unit. According to one embodiment the air bubble alarm system compares a value based on output from a first glucose sensor with a value based on output from a second glucose sensor, or a value based on output from said first lactate sensor with a value based on output from said second lactate sensor. The alarm system is adapted to be triggered if the difference between the values from the first and second sensors is on or above a predefined value. If the height of the flow channel of the sensor is low, there is a high possibility that an air bubble will be deformed, since there is little space available for the air bubble, and for a shallower flow channel a higher force is exerted on an air bubble. In that way the air bubble becomes destabilized and dissolves. If an air bubble would be present on the surface of a measuring electrode it would reduce the diffusion of the analyte down through the measuring electrode and result in an erroneous reading.

However, if an air bubble would be so large that it covers the whole, or substantially the whole, area of a measuring electrode the value recorded by the measuring electrode would drop rapidly, possibly to approximately zero depending on how long the air bubble would stay on the surface of the electrode, such a reading can be identified as erroneous and be discarded.

The system could further comprises a calculation unit, adapted to calculate a first ratio based on a first value and a second value, the first and second values being values based on the level of glucose, lactate and/or pyruvate in the analyte.

Please note that any embodiment or part of embodiment as well as any method or part of method could be combined in any way. All examples herein should be seen as part of the general description and therefore possible to combine in any way in general terms.

The invention claimed is:

1. A medical monitoring system for continuous monitoring of the glucose level and the lactate level of a critical care patient, wherein the monitoring system comprises:
    a display unit,
    a microdialysis or ultrafiltration catheter comprising an intracorporeal membrane,
    a first extracorporeal sensor in connection with the catheter, said sensor comprising at least one glucose electrode, at least one lactate electrode, and at least first and second blank electrodes, wherein in the direction of liquid flow past the sensor, the first blank electrode precedes the glucose electrode and the lactate electrode, and the second blank electrode follows the glucose electrode and the lactate electrode,
    a first unit, connected to the sensor and the display unit, adapted to:
        receive a first glucose signal based on the level of glucose in an analyte from the patient measured by the sensor,
        transform the glucose signal into a graphically displayable glucose signal, and
        transmit the graphically displayable glucose signal to the display unit of the monitoring system,
    a second unit, connected to the sensor and the display unit, adapted to:
        receive a first lactate signal based on the level of lactate in an analyte from the patient measured by the sensor,
        transform the lactate signal into a graphically displayable lactate signal, and
        transmit the graphically displayable lactate signal to the display unit of the monitoring system,
    an alarm system related to at least one of the glucose value and the lactate value, wherein the alarm system has a definable threshold value and is adapted to be triggered by a glucose or lactate value being above, on or below the threshold value, and
    a cross-talk alarm system related to cross-talk between the first blank electrode and the second blank electrode, wherein the cross-talk alarm system has a first predefined cross-talk threshold value and is adapted to be triggered by a difference between first and second values, based on signals from the first blank electrode and the second blank electrode, the difference being greater than the first predefined cross-talk threshold value.

2. The medical monitoring system according to claim 1, wherein the monitoring system further comprises a user operable switch having a first and second state, wherein the switch is adapted to:
  in the first state, enable the display unit to display the graphically displayable glucose signal, and
  in the second state, enable the display unit to display the graphically displayable lactate signal.

3. The medical monitoring unit according to claim 1, wherein the monitoring system is adapted to display the graphically displayable glucose signal and the graphically displayable lactate signal simultaneously.

4. The medical monitoring system according to claim 1, wherein the monitoring system further comprises a third unit, connected to the sensor and the display unit, adapted to:
  receive a first pyruvate signal based on the level of pyruvate in an analyte from the patient measured by the sensor,
  transform the pyruvate signal into a graphically displayable pyruvate signal, and
  transmit the graphically displayable pyruvate signal to the display unit of the monitoring unit.

5. The medical monitoring system according to claim 4, wherein the monitoring system further comprises a user operable switch having a first, second and third state, wherein the switch is adapted to:
  in the first state enable the display unit to display the graphically displayable glucose signal,
  in the second state, enable the display unit to display the graphically displayable lactate signal, and
  in the third state, enable the display unit to display the graphically displayable pyruvate signal.

6. The medical monitoring system according to claim 4, wherein the monitoring system is adapted to display:
  the graphically displayable glucose signal,
  the graphically displayable lactate signal, and
  the graphically displayable pyruvate signal simultaneously.

7. The medical monitoring system according to claim 4, wherein the monitoring system is adapted to update at least one of: the graphically displayable glucose signal, the graphically displayable lactate signal, and the graphically displayable pyruvate signal, with an interval shorter than 10 seconds.

8. The medical monitoring system according to claim 4, wherein the monitoring system further comprises a calculation unit adapted to:
  receive a lactate signal based on the level of lactate in an analyte from the patient measured by the sensor,
  receive a pyruvate signal based on the level of pyruvate in an analyte from the patient measured by the sensor,
  calculate a second ratio based on the lactate signal and the pyruvate signal,
  transform the second ratio into a graphically displayable second ratio signal, and
  transmit the graphically displayable second ratio signal to the display unit of the monitoring system.

9. The medical monitoring system according to claim 8, wherein the medical monitoring system further comprises an alarm system related to the second ratio, and wherein the alarm system is adapted to have a definable second ratio threshold value, and wherein the alarm system is adapted to be triggered by the second ratio being above, on or below the second ratio threshold value.

10. The medical monitoring unit according to claim 4, wherein the third unit is further adapted to:
  receive a second pyruvate signal based on a measured pyruvate value,
  calculate a mean pyruvate signal based on the first pyruvate signal and the second pyruvate signal,
  transform the mean pyruvate signal into a graphically displayable mean pyruvate signal, and
  transmit the graphically displayable mean pyruvate signal to the display unit of the monitoring unit.

11. The monitoring system according to claim 4, wherein the monitoring system further comprises a calculation unit, and wherein the calculation unit is adapted to receive a first pyruvate signal at a first instance in time, and receive a second pyruvate signal at a second instance in time, and wherein the calculation unit is adapted to calculate a mean pyruvate value from the first and second pyruvate signals.

12. The monitoring system according to claim 4, wherein the system further comprises a second sensor and a calculation unit and wherein the calculation unit is adapted to receive the first pyruvate signal from the first sensor, and to receive a second pyruvate signal from the second sensor, and wherein the calculation unit is adapted to calculate a mean pyruvate value from the first pyruvate signal and the second pyruvate signal.

13. The monitoring system according to claim 4, wherein the sensor comprises consecutively the first blank electrode, a first lactate electrode, a first glucose electrode, a first pyruvate electrode, the second blank electrode, a second lactate electrode, a second glucose electrode and a second pyruvate electrode.

14. The medical monitoring system according to claim 1, wherein the monitoring system further comprises a calculation unit adapted to:
  receive a glucose signal based on the level of glucose in an analyte from the patient measured by the sensor,
  receive a lactate signal based on the level of lactate in an analyte from the patient measured by the sensor,
  calculate a first ratio based on the glucose signal and the lactate signal,
  transform the first ratio into a graphically displayable first ratio signal, and
  transmit the graphically displayable first ratio signal to the display unit of the monitoring system.

15. The medical monitoring system according to claim 14, wherein the medical monitoring system further comprises an alarm system related to the first ratio, and wherein the alarm system is adapted to have a definable first ratio threshold value, and wherein the alarm system is adapted to be triggered by the first ratio being above, on or below the first ratio threshold value.

16. The medical monitoring system according to claim 1, wherein the medical monitoring system further comprises an alarm system related to a pyruvate value, and wherein the alarm system is adapted to have a definable pyruvate threshold value, and wherein the alarm system is adapted to be triggered by the pyruvate value being above or below the pyruvate threshold value.

17. The medical monitoring system according to claim 1, wherein the first unit is further adapted to:
  receive a second glucose signal based on a measured glucose value,
  calculate a mean glucose signal based on the first glucose signal and the second glucose signal, transform the mean glucose signal into a graphically displayable mean glucose signal, and transmit the graphically displayable mean glucose signal to the display unit of the monitoring unit.

18. The medical monitoring system according to claim 1, wherein the second unit is further adapted to:
receive a second lactate signal based on a measured lactate value,
calculate a mean lactate signal based on the first lactate signal and the second lactate signal,
transform the mean lactate signal into a graphically displayable mean lactate signal, and
transmit the graphically displayable mean lactate signal to the display unit of the monitoring unit.

19. The monitoring system according to claim 1, wherein the monitoring system further comprises a calculation unit, and wherein the calculation unit is adapted to receive a first glucose signal at a first instance in time, and receive a second glucose signal at a second instance in time, and wherein the calculation unit is adapted to calculate a mean glucose value from the first and second glucose signals.

20. The monitoring system according to claim 1, wherein the monitoring system further comprises a calculation unit, and wherein the calculation unit is adapted to receive a first lactate signal at a first instance in time, and receive a second lactate signal at a second instance in time, and wherein the calculation unit is adapted to calculate a mean lactate value from the first and second lactate signals.

21. The monitoring system according to claim 1, wherein the monitoring system further comprises a second sensor and a calculation unit, and wherein the calculation unit is adapted to receive the first glucose signal from the first sensor, and to receive a second glucose signal from the second sensor, and wherein the calculation unit is adapted to calculate a mean glucose value from the first glucose signal and the second glucose signal.

22. The monitoring system according to claim 1, wherein the system further comprises a second sensor and a calculation unit, and wherein the calculation unit is adapted to receive the first lactate signal from the first sensor, and to receive a second lactate signal from the second sensor, and wherein the calculation unit is adapted to calculate a mean lactate value from the first lactate signal and the second lactate signal.

23. The monitoring system according to claim 1, wherein the sensor comprises at least two lactate electrodes and at least two glucose electrodes.

24. The monitoring system according to claim 1, further comprising a projection alarm system related to a projected value of at least one of:
the glucose value,
the lactate value, and
a the pyruvate value, and
wherein the projection alarm system has a definable projected threshold value, and wherein the projection alarm system is adapted to be triggered by a projected glucose value, a projected lactate value or a projected pyruvate value being above, on or below the definable projected threshold value.

25. A method of using a microdialysis or ultrafiltration catheter for continuously monitoring a glucose level and a lactate level of a critical care patient, wherein the method comprises the steps of:
obtaining a liquid flow of analyte through an intracorporeal membrane into the catheter,
transporting the liquid flow of analyte from the catheter to an extracorporeal sensor, wherein the extracorporeal sensor is capable of sensing glucose and lactate and comprises at least one glucose electrode, at least one lactate electrode, and at least first and second blank electrodes, wherein in the direction of liquid flow past the sensor, the first blank electrode precedes the glucose electrode and the lactate electrode, and the second blank electrode follows the glucose electrode and the lactate electrode,
measuring the glucose level at the extracorporeal sensor,
receiving, at a first unit, a first glucose signal based on the measured level of glucose,
transforming the glucose signal to a graphically displayable glucose signal, and
transmitting the graphically displayable glucose signal to a display unit,
measuring the lactate level at the extracorporeal sensor,
receiving, at a second unit, a first lactate signal based on the measured level of lactate,
transforming the lactate signal into a graphically displayable lactate signal, and
transmitting the graphically displayable lactate signal to the display unit, and
receiving a first signal from the first blank electrode,
receiving a second signal from the second blank electrode,
converting the first signal and the second signal into a first value and a second value,
comparing the first value and the second value, and
detecting if the difference between the first value and second value is equal to or larger than a first predefined cross-talk threshold, and triggering a crosstalk signal when the difference is equal to or larger than the first predefined cross-talk threshold value.

26. The method according to claim 25, wherein the method further comprises the step of displaying, at the display unit, the graphically displayable glucose signal and the graphically displayable lactate signal simultaneously.

27. The method according to claim 25, wherein the method further comprises the step of:
measuring a pyruvate level at the extracorporeal sensor,
receiving at a third unit, a first pyruvate signal based on the measured level of pyruvate,
transforming the pyruvate signal into a graphically displayable pyruvate signal, and
transmitting the graphically displayable pyruvate signal to the display unit.

28. The method according to claim 27, wherein the method further comprises the step of displaying: the graphically displayable glucose signal, the graphically displayable lactate signal, and the graphically displayable pyruvate signal simultaneously.

29. The method according to claim 27, wherein the method further comprises the step of updating at least one of: the graphically displayable glucose signal, the graphically displayable lactate signal, and the graphically displayable pyruvate signal, with an interval shorter than 10 seconds.

30. The method according to claim 27, wherein the method further comprises the steps of:
receiving, at a calculation unit, a lactate signal based on the measured level of lactate,
receiving, at the calculation unit, a pyruvate signal based on the measured level of pyruvate,
calculating, at the calculation unit, a first ratio based on the lactate signal and the pyruvate signal,
transforming the first ratio into a graphically displayable first ratio signal, and transmitting the graphically displayable first ratio signal to the display unit.

31. The method according to claim 27, wherein the method further comprises the steps of:
receiving, at a third unit, a second pyruvate signal based on a measured pyruvate value,
calculating a mean pyruvate signal based on the first pyruvate signal and the second pyruvate signal,
transforming the mean pyruvate signal into a graphically displayable mean pyruvate signal, and
transmitting the graphically displayable mean pyruvate signal to the display unit.

32. The method according to claim 27, wherein the method further comprises the steps of:
receiving, at a calculation unit, a first pyruvate signal at a first instance in time,
receiving, at the calculation unit, a second pyruvate signal at a second instance in time, and
calculating, at the calculation unit, a mean pyruvate value from the first and second pyruvate signals.

33. The method according to claim 27, wherein the method further comprises the steps of:
receiving, at a calculation unit, a first pyruvate signal from the sensor,
receiving, at the calculation unit, a second pyruvate signal from the sensor, and
calculating, at the calculation unit, a mean pyruvate value from the first pyruvate signal and the second pyruvate signal.

34. The method according to claim 27, wherein the sensor comprises consecutively the first blank electrode, a first lactate electrode, a first glucose electrode, a first pyruvate electrode, the second blank electrode, a second lactate electrode, a second glucose electrode and a second pyruvate electrode.

35. The method according to claim 25, wherein the method further comprises the steps of:
receiving, at a calculation unit, a glucose signal based on the measured level of glucose,
receiving, at the calculation unit, a lactate signal based on the measured level of lactate,
calculating, at the calculation unit, a first ratio based on the glucose signal and the lactate signal,
transforming the first ratio into a graphically displayable first ratio signal, and
transmitting the graphically displayable first ratio signal to the display unit.

36. The method according to claim 25, wherein the method further comprises the step of setting an alarm system related to a threshold value of at least one of:
the glucose level,
the lactate level, and
a pyruvate level,
such that the alarm system is triggered by the at least one level being above or below the threshold value.

37. The method according to claim 25, wherein the method further comprises the step of setting a projection alarm system related to a threshold level of at least one of:
the glucose level,
the lactate level, and
a pyruvate level,
such that the alarm system is triggered by the at least one level being above or below the threshold level.

38. The method according to claim 25, wherein the method further comprises the steps of transmitting at least one of: the glucose signal, the lactate signal and a pyruvate signal to a central system.

39. The method according to claim 25, wherein the method further comprises the steps of:
receiving, at the first unit, a second glucose signal based on a measured glucose value,
calculating a mean glucose signal based on the first glucose signal and the second glucose signal,
transforming the mean glucose signal into a graphically displayable mean glucose signal, and
transmitting the graphically displayable mean glucose signal to the display unit.

40. The method according to claim 25, wherein the method further comprises the steps of:
receiving at the second unit, a second lactate signal based on a measured lactate value,
calculating a mean lactate signal based on the first lactate signal and the second lactate signal,
transforming the mean lactate signal into a graphically displayable mean lactate signal, and
transmitting the graphically displayable mean lactate signal to the display unit.

41. The method according to claim 25, wherein the method further comprises the steps of:
receiving, at a calculation unit, a first glucose signal at a first instance in time,
receiving, at the calculation unit, a second glucose signal at a second instance in time, and
calculating, at the calculation unit, a mean glucose value from the first and second glucose signals.

42. The method according to claim 25, wherein the method further comprise the steps of:
receiving, at a calculation unit, a first lactate signal at a first instance in time,
receiving, at the calculation unit, a second lactate signal at a second instance in time, and
calculating, at the calculation unit, a mean lactate value from the first and second lactate signals.

43. The method according to claim 25, wherein the method further comprises the steps of:
receiving, at a calculation unit, a first glucose signal from the sensor,
receiving, at the calculation unit, a second glucose signal from the sensor, and
calculating, at the calculation unit, a mean glucose value from the first glucose signal and the second glucose signal.

44. The method according to claim 25, wherein the method further comprises the steps of:
receiving, at a calculation unit, a first lactate signal from the sensor,
receiving, at the calculation unit, a second lactate signal from the sensor, and
calculating, at the calculation unit, a mean lactate value from the first lactate signal and the second lactate signal.

45. The method according to claim 25, wherein the sensor comprises at least two lactate electrodes and at least two glucose electrodes.

* * * * *

UNITED STATES PATENT AND TRADEMARK OFFICE
CERTIFICATE OF CORRECTION

PATENT NO. : 9,763,610 B2  
APPLICATION NO. : 13/519943  
DATED : September 19, 2017  
INVENTOR(S) : Anton Karlsson et al.

Page 1 of 1

It is certified that error appears in the above-identified patent and that said Letters Patent is hereby corrected as shown below:

On the Title Page

Item "(73) Assignee" change "MB," to --AB,--.

Signed and Sealed this  
Twenty-sixth Day of December, 2017

Joseph Matal  
*Performing the Functions and Duties of the*  
*Under Secretary of Commerce for Intellectual Property and*  
*Director of the United States Patent and Trademark Office*